(12) United States Patent
Fisher

(10) Patent No.: US 6,214,544 B1
(45) Date of Patent: *Apr. 10, 2001

(54) METHOD TO IDENTIFY TUMOR SUPPRESSOR GENES

(75) Inventor: Paul B. Fisher, Scarsdale, NY (US)

(73) Assignee: The Trustees of Columbia University, New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/750,556
(22) PCT Filed: Jun. 15, 1995
(86) PCT No.: PCT/US95/07738
   § 371 Date: Mar. 27, 1997
   § 102(e) Date: Mar. 27, 1997
(87) PCT Pub. No.: WO95/34680
   PCT Pub. Date: Dec. 21, 1995

Related U.S. Application Data

(63) Continuation-in-part of application No. 08/260,326, filed on Jun. 15, 1994, now abandoned.

(51) Int. Cl.$^7$ ............... C12Q 1/68; C07H 21/02; C07H 21/04
(52) U.S. Cl. ............... 435/6; 536/23.1; 536/24.3
(58) Field of Search ............... 435/6; 935/76, 935/77; 536/23.1, 24.3

(56) References Cited

U.S. PATENT DOCUMENTS 5,217,889 * 6/1993 Roninson et al. .
5,811,234 * 9/1998 Roninson et al. .

OTHER PUBLICATIONS

Chen et al., Molecular and Cellular Biology 7(8): 2745–2752 (1987).*
Davis et al., Basic Methods in Molecular Biology, pp.296–297, Elsevier Science Publishing Co., New York, New York (1986).*
Deiss et al., Science 252 :117–120 (1991).*
Holzmayer et al., Nucleic Acids Research 20 :711–717 (1992).*
Artelt, P. et al., (1991) The prokaryotic neomycin–resistance–encoding gene acts as a transcriptional silencer in eukaryotic cells. *Gene*, 99:249–254.
Babiss, L.E. et al., (1986) Mutations in the E1a gene of adenovirus type 5 alter the tumorigenic properties of transformed cloned rat embryo fibroblast cells. *Proc. Natl. Acad. of Sci.*, 83:2167–2171.
Bishop, J.M., (1987) The molecular genetics of cancer. *Science*, 235:305–311.

Boylon, J.F. et al., (1990) Role of the Ha–ras (ras$^H$) oncogene in mediating progression of the tumor cell phenotype. *Anticancer Research*, 10:717–724.
Boylon, J.F. et al., (1992) Induction and progression of the transformed phenotype in cloned rat embryo fibroblast cells: studies employing type 5 adenovirus and wild–type and mutant Ha–ras oncogenes. *Mol. Carcinogenesis*, 5:118–128.
Dreher, K.L. and Cowan, K., (1991) Expression of antisense transcripts encoding an extracellular matrix protein by stably transfected vascular smooth muscle cells. *European J. of Cell Biol.*, 54:1–9.
Fisher, P.B. et al., (1982) Analysis of type 5 adenovirus transformation with a cloned rat embryo line (CREF). *Proc. Natl. Acad. of Sci.*, 79:3527–3531.
Fisher, P.B. et al., (1984) Enhancement of viral transformation and expression of the transformed phenotype by tumor promoters. In: Tumor Promotion and Carcinogenesis In Vitro, Mechanisms of Tumor Promotion, T.J. Slaga (ed.), Florida, CRC Press, pp. 57–123.
Fisher, P.B. and Rowley, P.T., (1991) Regulation of growth, differentiation and antigen expression in human tumor cells by recombiant cytokines: Application for the differentiation therapy of human cancer *The Status of Differentiation Therapy of Cancer*, S. Waxman et al. (Eds.), New York, Raven Press, pp. 201–213.
Frenkel, K. et al., (1993) Inhibition of tumor promoter–mediated processes in mouse skin and bovine lens by caffeic acid phenethyl ester, *Cancer Research*, 53:1255–1261.
Glover, D. et al., (1989) Discloses that K–ras and Ki–ras are equivalent. "Oncogenes", *Oxford University Press*, p. 217.
Gudkov, A.V. et al., (1994) Cloning mammalian genes by expression selection of genetic suppressor elements: Association of Kinesin with drug resistance and cell immortalization. *Proc. Natl. Acad. of Sci. USA*, 91:3744–3748.
Huang et al., (1988) Suppression of the neoplastic phenotype by replacement of the RB gene in human cancer cells. *Science*, 242:1563–1566.

(List continued on next page.)

Primary Examiner—Ethan Whisenant
(74) *Attorney, Agent, or Firm*—John P. White; Cooper & Dunham LLP

(57) ABSTRACT

This invention provides a method of identifying a tumor suppressor gene of a cell(s). Analogous methods to identify tumor suppressors in normal cells and to identify genes associated with unknown genetic defects are also described. The feasibility of the title method was demonstrated by observing the effects of caffeine acid phenethyl ester on oncogene-tranformed CREF cells. In a second series of expts., human papillomavirus 18-transformed CREF cells were transfected with human fibroblast cDNA cloned into a pMAM-neo vector which allows dexamethasone-inducible expression. After growth in the presence of G418, neomycin resistant transformed CREF cells were obsd. Application of dexamethasone resulted in appearance of cells with normal phenotype.

21 Claims, 23 Drawing Sheets

OTHER PUBLICATIONS

Hu, M.C.-T. and Davidson, N., (1990) A combination of depression of the lac operator–repressor system with positive induction by glucocorticoid and metal ions provides a high–level–inducible gene expression system based on the human metallothionein–$II_A$ promoter. *Mol. and Cellular Biol.*, 10;6141–6151.

Johansen, T.E. et al., (1990) Biosynthesis of peptide precursors and protease inhibitors using new constitutive and inducible eukaryotic expression vectors. *FEBS*, 267:289–294.

Kitayama, H. et al., (1989) A ras–related gene with transformation suppressor activity. *Cell*, 56:77–84.

Lee et al., (1981) Glucocorticoids regulate expression of dihydrofolate reductase cDNA in mouse mammary tomour virus chimaeric plasmids, *Nature*, 294:228–232.

Levine, A.J. et al., (1993) The tumor suppressor genes. *Ann. Rev. of Biochem.*, 62:623–651.

Lin, J. et al., (1994) Expression of the transformed phenotype induced by diverse acting viral oncogenes mediates sensitivity to growth suppression induced by caffeic acid phenethyl ester (CAPE). *Intl. J. of Oncology*, 4:1–11.

Liotta, L.A. et al., (1991) Review of cancer metastasis and angiogenesis: an imbalance of positive and negative regulation. *Cell*, 64:327–336.

Marshall, C.J. Tumor suppressor genes. *Cell*, 64:313–326.

von Melchner, H. et al., (1990) Isolation of cellular promoters by using a retrovirus promoter trap. *Proc. Natl. Acad. of Sci.*, 87:3635–4022.

Noda, M. et al., (1983) Flat revertants isolated from Kirsten sarcoma virus–transformed cells are resistant to the action of specific oncogenes. *Proc. Natl. Acad. of Sci.*, 80:5602–5606.

Noda, M. et al., (1989) Detection of genes with a potential for suppressing the transformed phenotype associated with activated ras genes. *Proc. Natl. Acad. of Sci.*, 86:162–166.

Reid, L.H. et al., (1991) Cotransformation and gene targeting in mouse embryonic stem cells. *Mol. and Cellular Biol.*, 11:2769–2777.

Scharfmann, R. et al., (1991) Long–term in vivo expression of retrovirus–mediated gene transfer in mouse fibroblast implants. *Proc. Natl. Acad. of Sci. USA*, 88:4565–5066.

Su, Z–z. et al., (1993) Defining the critical gene expression changes associated with expression and suppression of the tumorigenic and metastatic phenotype in Ha–ras–transformed cloned rat embryo fibroblast cells. *Oncogene*, 8:1211–1219.

Su, Z–z. et al., (1993) Wild–type adenovirus type 5 transforming genes function as transdomaint suppressors of oncogenes is in mutant adenovirus type 5 transformed rat embryo fibroblast cells. *Cancer Res.*, 53:1929–1938.

Vousden, K., (1993) Interactions of human papillomavirus transforming proteins with the products of tumor suppressor genes. *FASEB J.*, 7:872–879.

Weinberg, R.A., (1991) Tumor suppressor genes. *Science*, 354:1138–1146.

\* cited by examiner

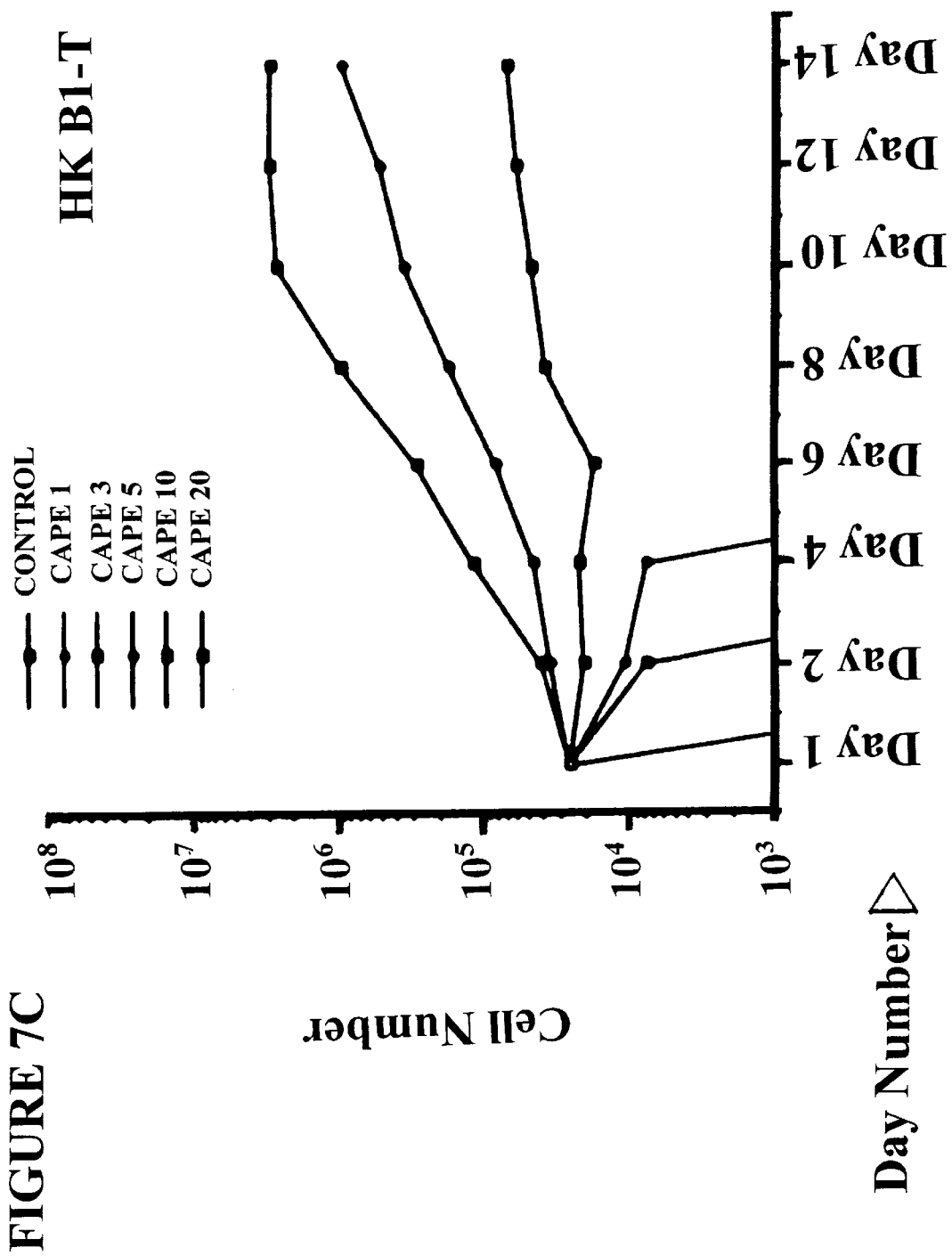

METHOD TO IDENTIFY TUMOR SUPPRESSOR GENES

This application is a 371 of PCT/US95/07738 filed Jun. 15, 1995 which is a continuation-in-part of U.S. application Ser. No. 08/260,326, filed Jun. 15, 1994 now abandoned, the contents of which are hereby incorporated by reference.

The invention disclosed herein was made with Government support under NCI/NIH Grant No. CA35675 from the Department of Health and Human Services. Accordingly, the U.S. Government has certain rights in this invention.

Throughout this application, various references are referred to by number within parentheses. Disclosures of these publications in their entireties are hereby incorporated by reference into this application to more fully describe the state of the art to which this invention pertains. Full bibliographic citation for these references may be found at the end of this application, preceding the claims.

BACKGROUND OF THE INVENTION

The carcinogenic process is complex and often involves changes in the expression of two contrasting genetic elements, i.e., positive acting oncogenes and negative acting anti-oncogenes (tumor suppressor genes) (for reviews see references 1–3). Compounds displaying selective toxicity toward transformed cells overexpressing different classes of oncogenes could prove useful as potential antitumor agents and as reagents for identifying cellular targets susceptible to modification by transforming oncogenes.

Cancer is often a consequence of changes in the expression of a number of genes. These include, dominant-acting oncogenes, tumor suppressor genes, genes affecting cell cycle and genes affecting genomic stability. In the case of tumor suppressor genes, the ability to identify and isolate these elements have proven difficult often involving extensive gene mapping and technically complex and many times unsuccessful molecular approaches. Prior to the art described in this invention, no simple and efficient way of identifying and cloning tumor suppressor genes has been available. The currently described approach is simple and effective in directly identifying potentially novel human tumor suppressor genes and directly cloning these genes. The approach, termed inducible suppression cDNA cloning, is useful in identifying both oncogene specific suppressor genes and global oncogene-independent tumor suppressor genes.

Current knowledge of tumor suppressor genes indicate that they often function as negative regulators of cell growth. Inherent in this operational definition of a tumor suppressor gene is the obvious implication that expression of a tumor suppressor gene in a target cell may evoke a loss of proliferative ability. This possibility has been demonstrated directly by reintroducing cloned tumor suppressor genes through DNA-transfection into tumor cells, i.e., growth and oncogenicity are suppressed. The growth inhibitory effect of tumor suppressor genes has prevented the previous development of functional assays permitting isolation of cells expressing novel tumor suppressor genes (anti-oncogenes).

SUMMARY OF THE INVENTION

This invention provides a method of identifying a tumor suppressor gene of a cell(s) which comprises the following steps: a) obtaining cDNA from a normal cell(s); b) preparing a library from the cDNA of step (a), wherein the cDNA is under the control of an inducible expression control system which also carries a selectable gene; c) introducing the vector library into a population of cell(s) expressing a transformed phenotype; d) placing the introduced transformed cell(s) from step (c) in conditions permitting expression of the cDNA and an effective concentration of an appropriate selection agent to select the cell(s) expressing the selectable gene; e) identifying the cell(s) which express the normal phenotype; and f) analyzing the cell(s) so identified so as to characterize the DNA and thus identify the tumor suppressor gene.

Analogous methods to identify tumor suppressors in normal cells and to identify genes associated with unknown genetic defects are also described.

The medium was exchanged and the appropriate concentration of CAPE added every 4–5 days. Results are the average for triplicate plates which varied by ≦10%.

FIGS. 7A, 7B, 7C and 7D illustrate the effect of CAPE on the growth of (A) Ha-ras- transformed CREF (Ha-ras), (B) Ha-ras plus Krev-1-transformed CREF (HK B1), (C) Ha-ras plus Krev-1-transformed nude mouse tumor-derived CREF (HK B1-T) and (D) Ha-ras plus Krev-1-transformed nude mouse lung metastasis-derived CREF (HK B1-M). Experimental details are as described in the legend to FIG. 6A–6D. Cell descriptions may be found in Materials and methods.

FIGS. 8A, 8B, 8C and 8D illustrate the effect of CAPE on H5hr1-transformed CREF (A2), a human fibroblast cDNA-induced H5hr1-transformed revertant A2 CREF clone (A2/Hu-Rev/cl 5), v-src-transformed CREF (v-src/cl 1) and a v-src-transformed flat revertant CREF clone (v-src/A2-Hu-Rev/cl 3). Experimental details are as described in the legend to FIG. 6. Cell descriptions may be found in Materials and methods.

Figure 9:
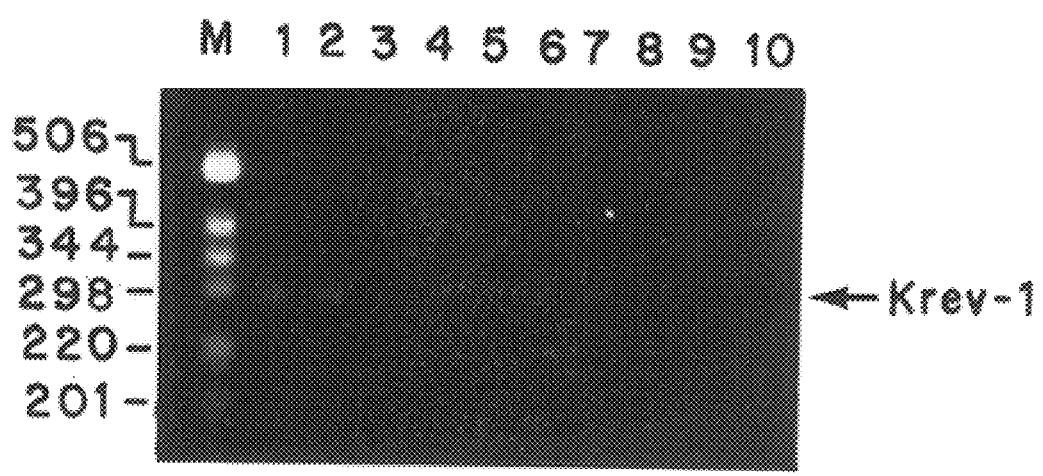

FIG. 9 illustrates the PCR amplification of the unique Krev-1 gene region from CREF, Ha-ras-transformed CREF, Ha-ras plus Krev-1-transformed CREF, Ha-ras plus Krev-1 nude mouse tumor-derived and Ha-ras plus Krev-1 metastasis-derived cells. Experimental details can be found in Materials and methods. Lane designations are as follows: M, DNA size-marker; 1, Ha-ras plus Krev-1 metastasis-derived clone, HK A3-M; 2, Ha-ras plus Krev-1 transformed clone, HK A3; 3, Ha-ras plus Krev-1 metastasis-derived clone, HK B2-M; 4, Ha-ras plus Krev-1 nude mouse tumor-derived clone, HK B2-T; 5, Ha-ras plus Krev-1 transformed clone, HK B2; 6, Ha-ras plus Krev-1 metastasis-derived clone, HK B1-M; 7, Ha-ras plus Krev-1 nude mouse tumor-derived clone, HK B1-T; 8, Ha-ras plus Krev-1 transformed clone, HK B1; 9, Ha-ras-transformed CREF; and 10, CREF.

Figure 10:
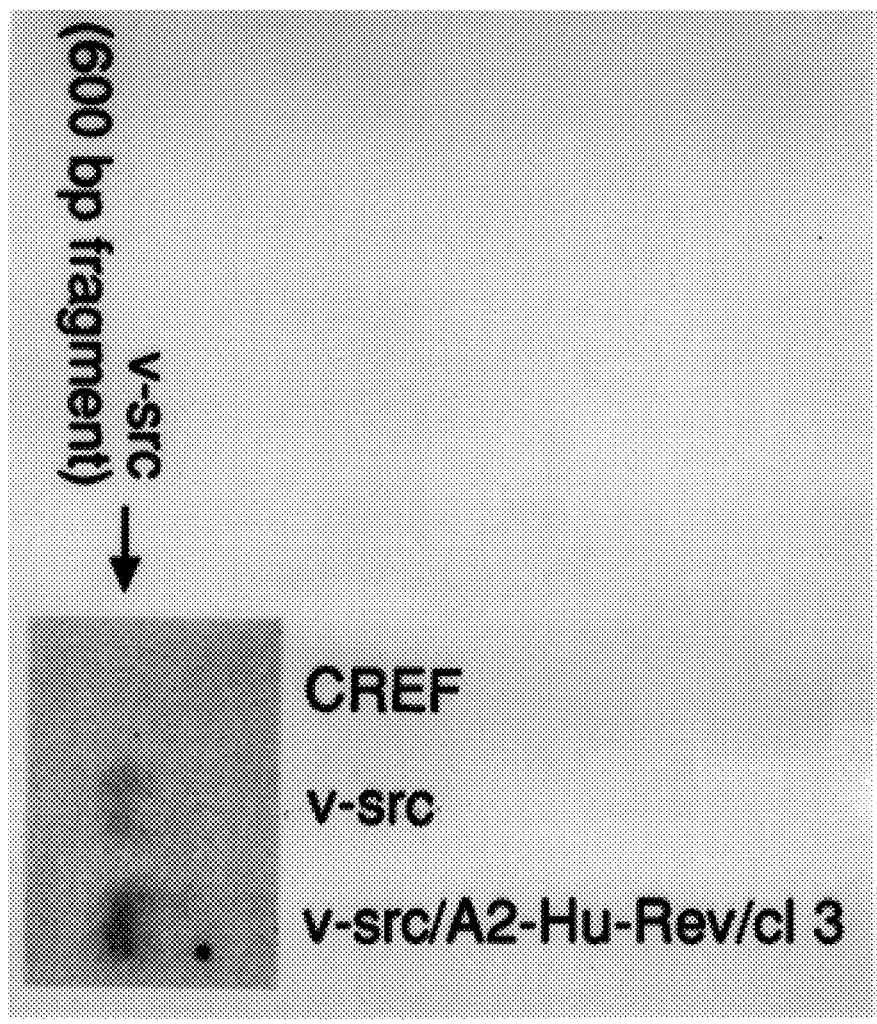

FIG. 10 illustrates DNA filter hybridization analysis of v-src in CREF, v-src-transformed CREF (v-src/cl 1) and v-src-transformed flat revertant CREF (v-src/A2-Hu-Rev/cl 3), Cellular DNA was cleaved with the restriction endonuclease PstI, 40 µg of DNA was electrophoresed on a 1% agarose gel, transferred to a nylon filter and hybridized with a multiprime $^{32}$P-labeled v-src probe.

Figure 11:
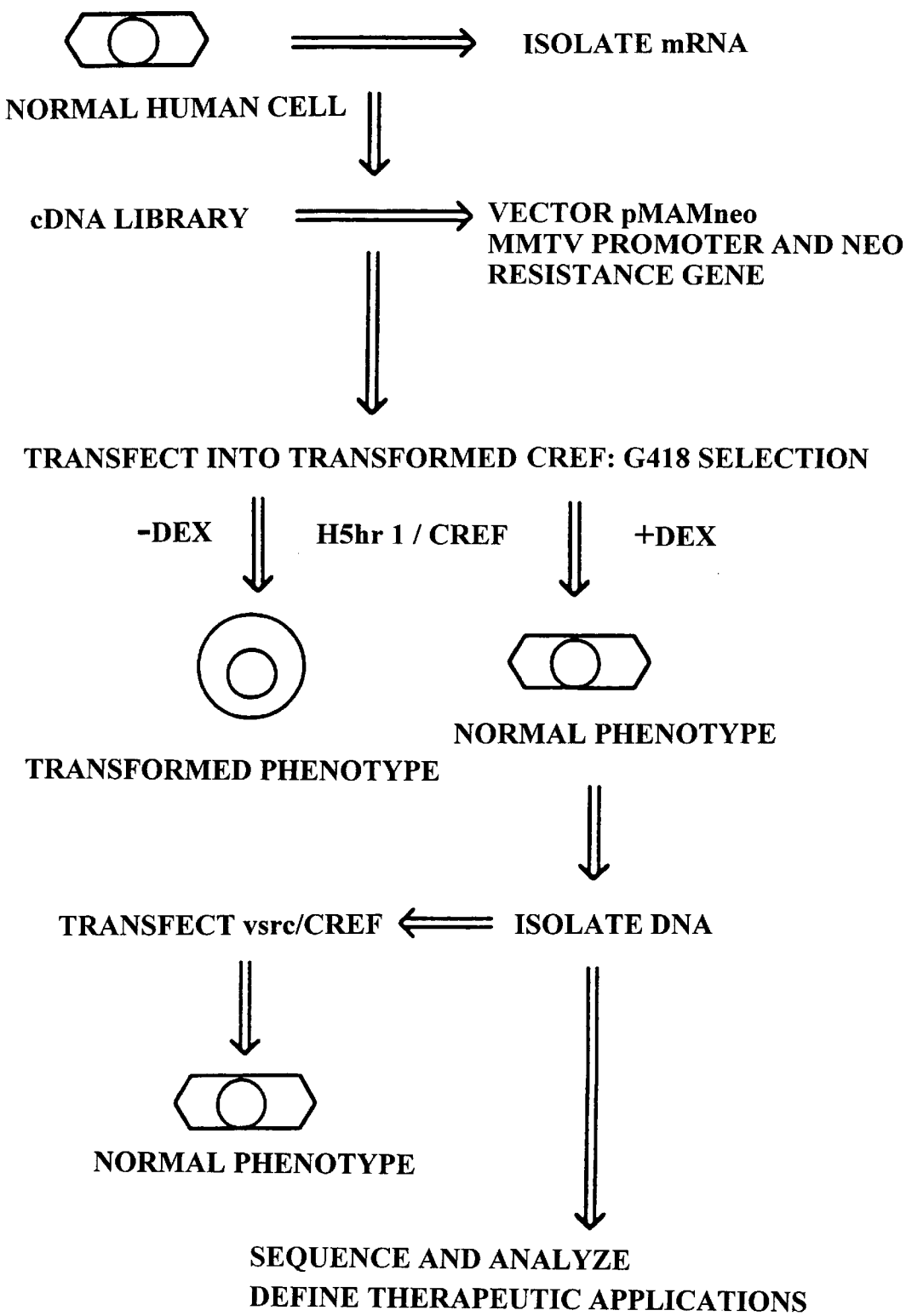

FIG. 11 illustrates a scheme for the inducible suppression of cDNA cloning.

Figure 12:
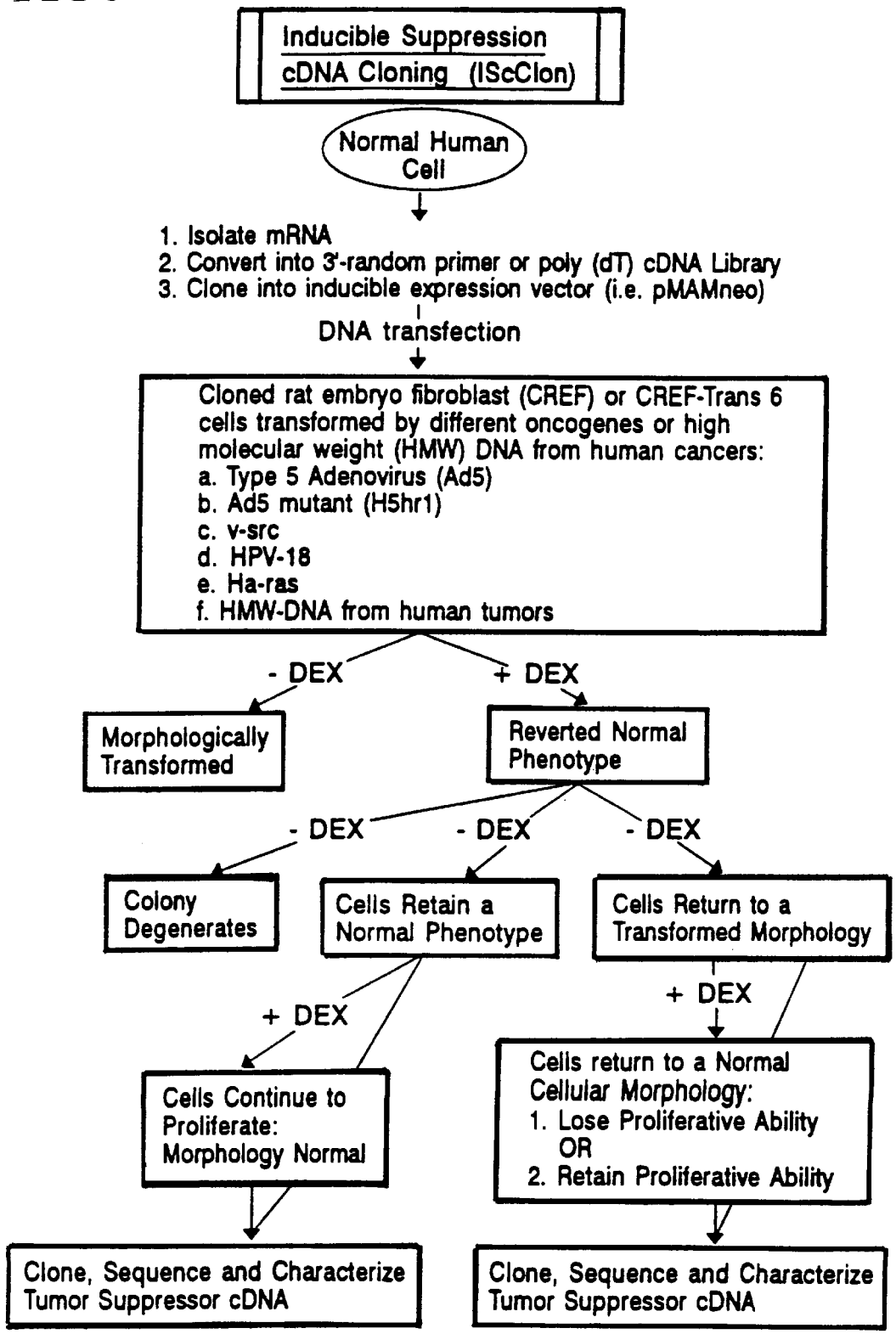

FIG. 12 illustrates a modified IscClon strategy.

Figure 13:
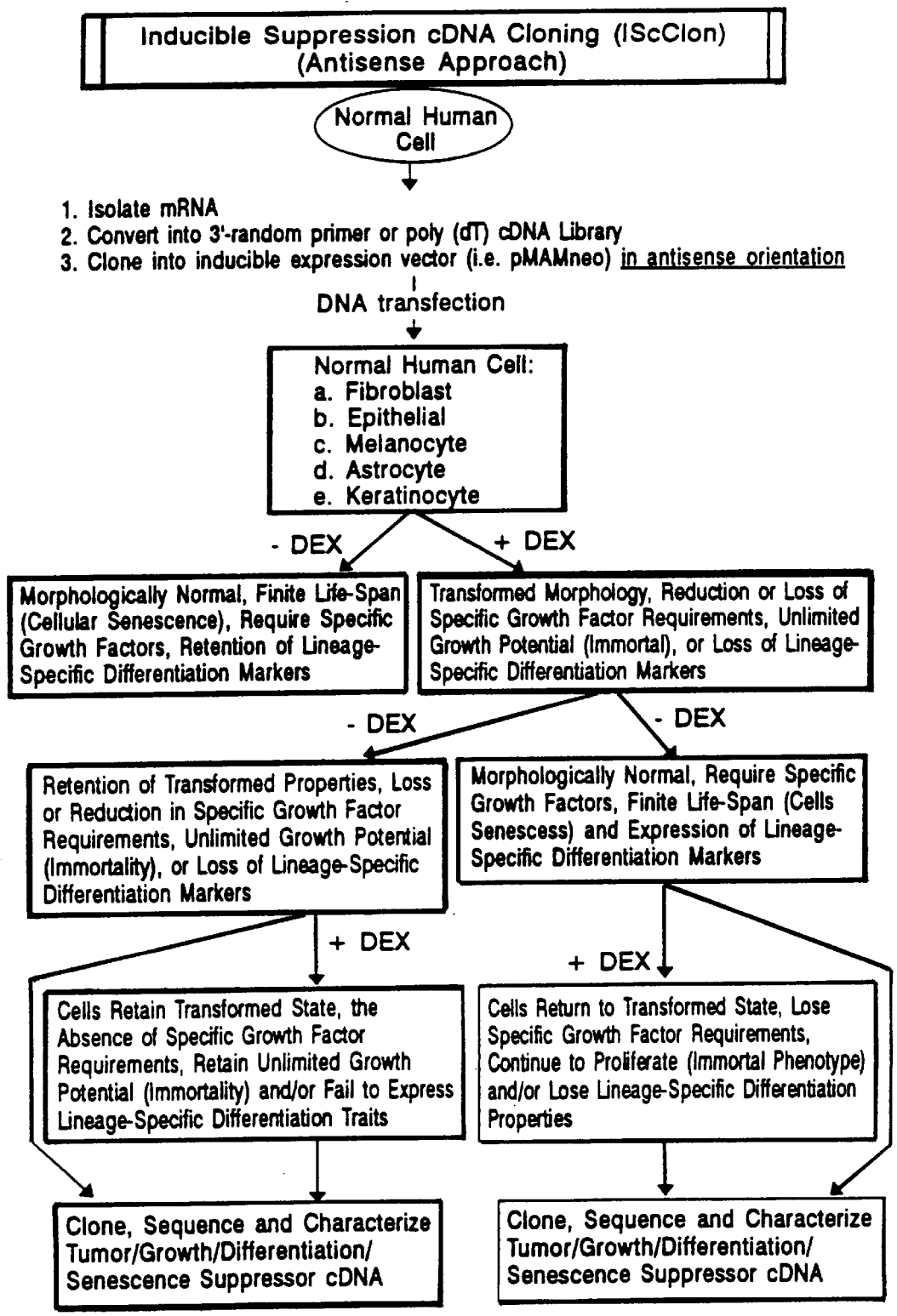

FIG. 13 illustrates a modified IscClon strategy (antisense approach).

Figure 14:
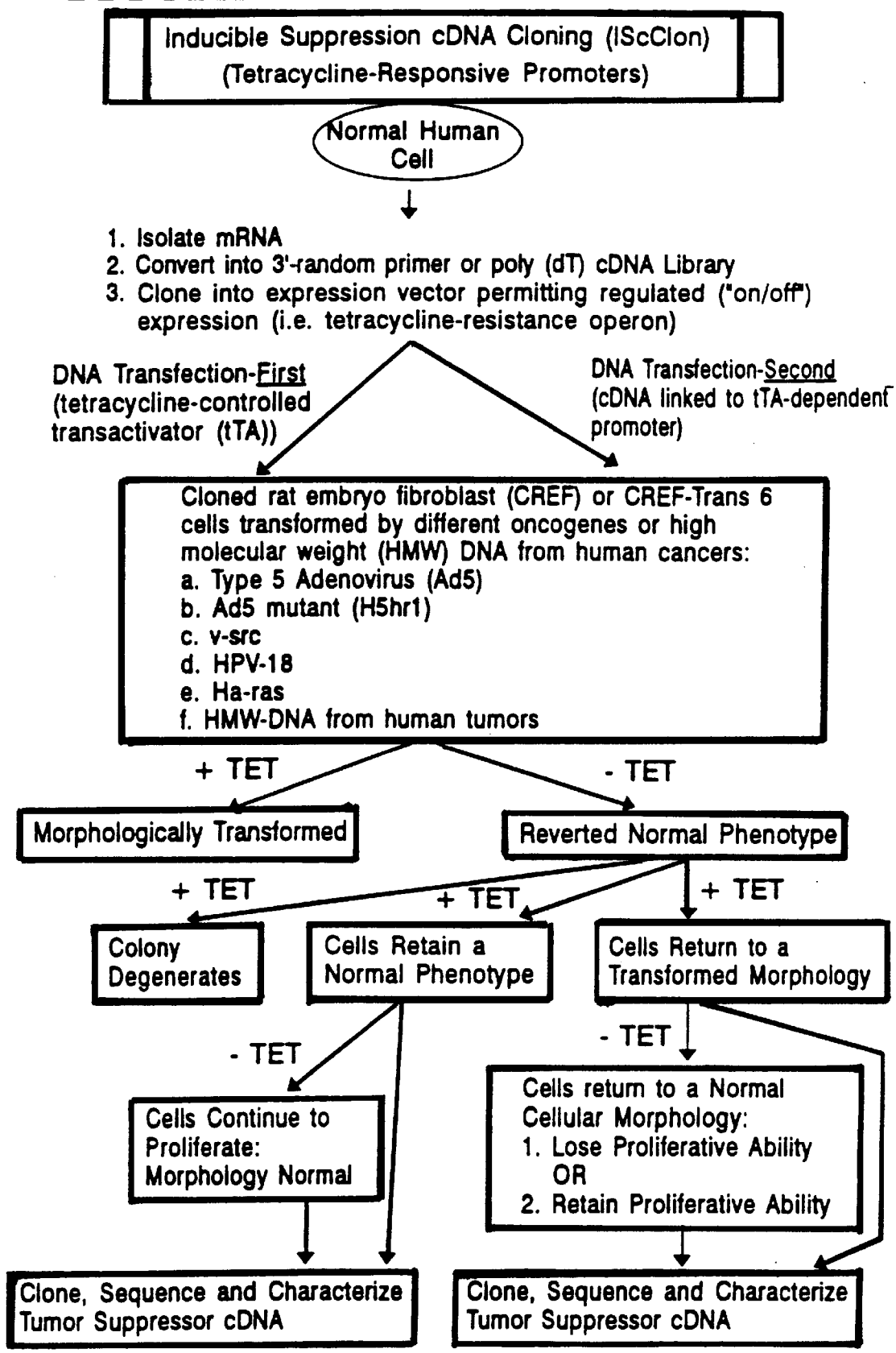

FIG. 14 illustrates a modified lscClon strategy (tetracycline responsive promoter).

DETAILED DESCRIPTION OF THE INVENTION

This invention provides a method of identifying a tumor suppressor gene of a cell(s) which comprises the following steps: a) obtaining cDNA or mRNA from a normal cell(s); b) preparing cDNA from the cell(s) if mRNA is obtained in step (a); c) preparing a library from the said cDNA, wherein the cDNA is under the control of an inducible expression control system which also carries a selectable gene; d) introducing the vector library into a population of cell(s) expressing a transformed phenotype; e) placing the introduced transformed cell(s) from step (d) in conditions permitting expression of the cDNA and an effective concentration of an appropriate selection agent to select the cell(s) expressing the selectable gene; f) identifying the cell(s) which express the normal phenotype; and g) analyzing the cell(s) so identified so as to characterize the DNA and thus identify the tumor suppressor gene.

In this invention, cDNA from normal cells may be obtained directly from the cells. First, targeted cells may be infected with retroviral vectors which carry appropriate primer. cDNA may now be synthesized within the cell. The synthesized cDNA can therefore be obtained directly from the cell.

In an embodiment of this invention, the inducible expression control system comprises an inducible promoter. In another embodiment, the inducible expression control system comprises a repressible promoter.

An alternative method of achieving controlled expression of genes involves the use of a modified tetracycline-repressible, bacterial tetracycline operator/repressor promoter system originally described by Gossen, M. and Bujard, H. ("Tight control of gene expression in mammalian cells by tetracycline-responsive promoters", Proc. Natl. Acad. Sci. USA, 89:5547–5551, 1992). This system uses two plasmid, pUHD15-1 and pUHD10-3. pUHD15-1 expresses a chimeric protein containing a tetracycline repressor fused to the activation domain of the herpes virus transcriptional activator, VP-16. The hybrid protein allows transactivation (tTA) of minimal promoters fused to the tetracycline operator sequences (tetO). Plasmid pUHD10-3 has a synthetic promoter with tandem repeats of a tetracycline operator (tetO) and a CMV-minimal promoter. The promoter in this plasmid is the target for activation by the tTA transcriptional activator. In the presence of tetracycline (1 µg/ml), this promoter is silent because tetracycline inhibits the ability of the tTA transactivator protein to bind to the tetO sequences. Elimination of tetracycline from the culture medium results in transcription of the gene controlled by this promoter in pUHD10-3. In this manner, cells containing the appropriate constructs can be experimentally manipulated to either express or not express normal human cDNAs by removal or addition of tetracycline. These constructs containing normal human cDNAs in an antisense orientation can be used to identify suppressor genes that when inhibited result in acquisition of a transformed phenotype by normal human cells. This approach can be applied directly to normal human cDNA libraries (either 3'-random primer cDNA or poly(dT) cDNA) (see below), cloned in a sense and antisense orientation, for use as part of the inducible suppression cDNA cloning (IScClon) strategy for identifying growth controlling and transformation suppressing tumor suppressor genes.

In one preferred embodiment of the method described above the cells expressing an transformed phenotype are CREF or CREF Trans 6 and may be transformed by either an adenovirus type 5 or the E1A region of the adenovirus type 5. In addition the cells expressing a transformed phenotype may also be transformed by an adenovirus or a retrovirus.

The transformed cells in step (c) of the method described above may be transformed by at least one oncogene or multiple oncogenes. The oncogene may be H-ras, K-ras, N-ras, v-src, v-raf, HPV-18 or HPV-51. The oncogene may be a membrane oncogene such as erb B1, erb B2, erb B3, c-fms, hst, kit, c-sis/PDGF-B and trk. Cytoplasmic oncogenes include c-abl, bcr, c-fes/fps, fyn, raf, ras and src. Other suitable oncogenes include nuclear oncogenes such as PRAD-1, erb-A, c-fos, c-jun, jun B, jum-D, mdm2-, c-myb, c-myc, B-myc, L-myc and N-myc.

A further embodiment of this invention is a method of identifying a tumor suppressor gene of a cell(s) which comprises the following steps: a) obtaining cDNA or mRNA from a normal cell(s); b) preparing cDNA from the cell(s) if mRNA is obtained in step (a); c) preparing an antisense library from the said cDNA, wherein the cDNA is under the control of an inducible expression control system which also carries a selectable gene; d) introducing the antisense library into a population of normal cell (s); e) placing the transfected normal cell(s) from step (d) in conditions permitting expression of the antisense cDNA and an effective concentration of an appropriate selection agent to select the cell(s) expressing the selectable gene; f) identifying the cell(s) which express the transformed phenotype; and g) analyzing the transformed cell(s) so identified so as to characterize the antisense cDNA and thus identify. the corresponding tumor suppressor gene.

In the methods described above the cell(s) identified in step (f) may be isolated and cultured under conditions so as to isolate and characterize the DNA and thus identify the tumor suppressor gene.

The invention provides for a method of identifying a gene in a cell(s) associated with an unknown genetic defect having a characteristic phenotype, which comprises the following steps: a) obtaining cDNA or mRNA from a normal cell(s); b) preparing cDNA from the cell if mRNA is obtained in step (a); c) preparing a library from the said cDNA, wherein the cDNA is under the control of an inducible expression control system which also carries a selectable gene; d) introducing the library into a population of cell(s) containing the unknown genetic defect having a characteristic phenotype; e) placing the cell(s) from step (d) in conditions permitting expression of the cDNA and an effective concentration of an appropriate selection agent to select the cell(s) expressing the selectable gene; f) identifying the cell(s) which express the a normal phenotype; and g) analyzing the cell(s) so identified so as to characterize the DNA and thus identify the gene associated with the unknown genetic defect. The cell(s) identified in step (f) may be isolated and cultured under conditions so as to isolate and characterize the DNA and thus identify the gene associated with the unknown genetic defect.

The gene in the cell(s) having an unknown genetic defect may be a cell(s) from a human tumor cell line or from primary human tumor isolates.

The unknown genetic defect may be associated with the following cancers, oral, esophagus, stomach, colon, rectum, liver, pancreas, larynx, lung, melanoma, skin, breast, cervix uteri, uterus, ovary, prostate, bladder, kidney, brain, non-hodgkin's lymphoma, hodbkin's disease, multiple myeloma and leukemia.

In one embodiment of the invention the inducer is removed from the cell(s) identified and isolated in step (e) prior to culturing the cell(s) in the methods described above. The inducible promoter may be $Zn^{2+}$ metallothionein promoter, metallothionein-1 promoter, human metallothionein IIA promoter, lac promoter, laco promoter, mouse mammary tumor virus early promoter, mouse mammary tumor virus LTR promoter, triose dehydrogenase promoter, herpes simplex virus thymidine kinase promoter, simian virus 40 early promoter or retroviral myeloproliferative sarcoma virus promoter.

In one preferred embodiment the inducible promoter is a mouse mammary tumor early virus promoter. The promoter may be contained in a plasmid, an adenoviral vector or a retroviral vector.

The selectable gene may be neomycin phosphotransferase, hygromycin, puromycin, G418 resistance, histidinol dehydrogenase or dihydrofolate reductase gene. One preferred embodiment of the invention is a selectable gene which is a neomycin phosphotransferase gene.

The tumor suppressor gene(s) identified by the methods described above may be operatively linked to a promoter of RNA transcription. Further embodiments of the invention include: a vector which comprises the tumor suppressor gene; a virus comprising the tumor suppressor gene; a polypeptide encoded by the tumor suppressor gene and an antibody capable of binding to the polypeptide.

Further embodiments of the invention include a non-human mammal whose germ cells or somatic cells contain a recombinant tumor suppressor gene introduced into the mammal at an embryonic stage. In additions the invention provides for a method of treating cells ex vivo which comprises contacting cells with the vector comprising the tumor suppressor gene so as to transform the cells and express the tumor suppressor gene discovered by the methods herein (see Leder, P. et al., U.S. Pat. No. 5,175,383, Krimpenfort, P. J. A. et al., U.S. Pat. No. 5,175,384, Wagner T. E. et al., U.S. Pat. No. 5,175,385 and U.S. Pat. No. 4,736,866).

As used herein the term identify or characterize the gene i.e. the tumor suppressor gene includes such methods of identification by fluorescence is situ hybridization, PCR, other nucleic acid probes and isolating, amplifying and sequencing such genes. Such methods are well known to those skilled in the art.

As used herein the term a gene associated with a unknown genetic defect means and includes a gene which causes a genetic defect. It includes also genes which are indicative or characteristic of a genetic defect.

The active component of the popular folk medicine propolis, caffeine acid phenethyl ester (CAPE) (5), displays increased toxicity toward cloned rat embryo fibroblast (CREF) cells transformed by adenovirus type 5 (Ad5) or the A5 E1A transforming gene versus untransformed CREF cells (5, 6). Employing CREF cells transformed by a cold-sensitive A5 E1A gene and an Ad5 E1A gene under the transcriptional control of a mouse mammary tumor virus promoter, evidence has been presented indicating that CAPE toxicity is a direct consequence of expression of the E1A-induced transformed phenotype (6). Transformation of the established rat embryo cell line, Rat 6, with the Ha-ras oncogene was also shown to increase the sensitivity of these cells to CAPE (6). CAPE and several additional caffeine acid esters inhibit azoxymethane-induced colonic preneoplastic lesions and ornithine decarboxylase, tyrosine protein kinase and lipoxygenase activities associated with colon carcinogenesis (7–9). In addition, CAPE exerts a dose-dependent growth suppressive effect on human colon adenocarcinoma, melanoma and glioblastoma multiforme cells (7, 10). In the human melanoma system, growth suppression was associated with the acquisition of morphological changes and the induction of cell surface antigenic changes suggesting a more differentiated phenotype (10). In contrast, at doses inducing growth suppression and cytoxicity in A5 E1A-transformed CREF or human tumor cells. CAPE was ineffective in altering the proliferative ability of normal human skin fibroblasts (6).

The mechanism by which CAPE induces its selective toxicity toward oncogene-transformed rodent cells and human tumor cells is not presently known. Further investigation of the phenomenon of CAPE-induced growth suppression and toxicity in oncogene-transformed rodent cells was of interest. For this invention CREF cells transformed by different classes of oncogenes have been employed. Evidence is presented indicating a direct relationship between CAPE sensitivity and transformation induced by diverse-acting oncogenes, including Ha-ras, HPV-18, HPV-51, v-raf and v-src. By using the Krev-1 tumor suppressor gene, which is 50% homologous to Ki-ras and blocks the transforming activity of Ha-ras and Ki-ras transformed cells at a post-transcriptional level (11–13), a direct relationship between expression of the transformed state, as opposed to the presence of the p21 Ha-ras oncogene-encoded protein, and CAPE sensitivity is also demonstrated. Additional studies have focused on human expression vector cDNA-library-induced revertant H5hr1- and v-src-transformed CREF cells that also display increased resistance to CAPE-induced toxicity versus their transformed counterparts. Taken together this indicate that the ability of CAPE to induce growth suppression and toxicity in transformed cells is a direct consequence of expression of the transformed phenotype as opposed to simply the presence of oncogene-encoded transforming proteins.

The technique of inducible suppression cDNA cloning eliminates these pitfalls and results in the isolation of tumor suppressor genes capable of suppressing the transformed and oncogenic phenotype of oncogene transformed cells. This approach that is outlined on FIG. 11 is based on the use of an inducible promoter to selectively regulate expression of a tumor suppressor gene. In the example shown, the promoter is a mouse mammary tumor virus long terminal repeat sequence that is responsive to dexamethasone (DEX). The same approach can be used in conjunction with promoters responsive to other agents, i.e., $Zn^{2+}$-inducible metallotheionein promoter, IPTG-inducible (Lacswitch, Stratagene) promoter, etc. By growing cells in DEX, transcription of the human cDNA stably integrated into the target cell genome is induced, whereas expression is extinguished when DEX is removed from the medium. This allows the identification (+DEX) (revertant flat morphology) and isolation (–DEX) (wild-type transformed morphology) of cells containing potential human tumor suppressor genes. By using target cells containing single or multiple oncogenes, or by multiple passage of the same cDNA tumor suppressor gene through cells containing different activated oncogenes, the currently described approach results in the identification of tumor suppressor genes with the capacity to revert specific oncogenic transforming events and/or tumor suppressor genes that can induce a global suppression of transformation (i.e., reversion of the transformed phenotype in cells containing different activated oncogenes, multiple activated oncogenes or undefined gene-induced or epigenic transformation related changes).

The current protocol should be very effective in isolating novel classes of tumor suppressor genes. Once identified, the novel tumor suppressor genes will prove valuable for numerous purposes. Including, designing gene-based strategies for reversing the oncogenic phenotype (adenoviral- or retroviral-based vectors carrying gene replacement constructs); identifying the proteins encoded by the novel tumor suppressor genes (enabling the development of potentially useful therapeutic reagents and diagnostic monoclonal antibodies); tumor screening and gene localization studies (diagnostic applications); and therapeutic intervention based on the development of rationally designed drugs capable of blocking specific biochemical pathways defective in cells displaying altered suppressor gene functions. By defining the precise genes and the encoded products involved in tumor suppression, it will also be possible to identify potentially novel and critical pathways mediating the neoplastic process. With this information in hand, it will be feasible to design more effective therapeutic modalities to treat cancer and to develop approaches (and reagents) to directly reverse the consequences of oncogene activation and tumor progression.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

First Series of Experiments

Materials and Methods
Caffeine Acid Phenethyl Ester
CAPE was synthesized as described by Grunberger et al. (5) and was kindly provided by Drs. T. Doyle and H. Wong, Bristol-Myers Squibb Co., Wallingford, Conn.
Cell Culture Systems
The CREF cell line is a clonal derivative of the F2408 Fischer rat embryo fibroblast cell line (14, 15). Ha-ras transformed CREF cells (Ha-ras) were obtained following transfection of CREF cells with the Ha-ras (T24) oncogene and isolating a focus of cells displaying a transformed morphology (16, 17). Ha-ras/Krev-1 cells, containing the Ha-ras and Krev-1 gene, were obtained by cotransfecting Ha-ras cells with a hygromycin resistance gene (pRSV1.1) (18) and selecting cells resistant to hygromycin and displaying a reversion in morphology to that of untransformed CREF cells (19). The Ha-ras/Krev-1 clone HK B1 was used (19). Additionally, an HK B1 nude mouse tumor-derived clone (HK B1-M) and a lung metastasis derived clone (HK B1-M) were analyzed for CAPE sensitivity (19). HPV-18- and HPV-51-transformed CREF cells were obtained following transfection with the cloned E6/E7 region of HPV-18 (20) and HPV-51 (21), respectively, and isolating morphologically transformed foci. CREF cells transformed by v-raf and v-src were obtained by transfecting CREF cells with the appropriate viral oncogene and isolating morphologically transformed foci (22, 23). A2 is a cold-sensitive host-range mutant, H5hr1, transformed CREF clone (24). A2 cells are tumorigenic in both nude mice and syngeneic rats (25, 26). Morphological revertant of A2 cells, such as A2/Hu-Rev/cl 5, were obtained following transfection with a human expression vector library constructed in the PMAM-neo vector. The cloned cDNA inducing reversion in morphology of A2 cells was isolated and transfected into v-src-transformed CREF in morphologically revertant v-src cells, such as v-src/A2-Hu-Rev/cl 3. All cell lines were grown in Dulbecco's modified Eagle's medium containing 5% fetal bovine serum (DMEM-5) at 37° C. in a 5% $CO_2$-95% air-humidified incubator.
Growth in Monolayer Culture and Anchorage-Independent Growth Assays
For monolayer growth, CREF and the various oncogene-transformed CREF cells were seeded at $2\times10^3/3.5$ cm plate, and approximately 16 hours later, the medium was exchanged and 0, 0.5, 1, 3, 5, 10 or 20 µg/ml CAPE added. Cell numbers from triplicate plates were determined at days 1, 2, 4, 6, 8 10, 12 and 14. The medium was exchanged and the appropriate concentration of CAPE added every 4–5 days. For agar cloning studies, cells were seeded at $1\times10^3$ and $5\times10^4$/6-cm plate in 0.4% Noble agar on a 0.8% Noble agar base layer, both containing DMEM-5. Cultures were refed every 4 days with 0.4% Noble agar containing DMEM-5. Colonies >0.1 mm in diameter were identified with a calibrated grid under an Olympus inverted phase-contrast microscope after 21 days.

PCR Analysis

To demonstrate the presence and retention of increased copies of the Krev-1 gene in the HK B1, HK B1-T and HK B1-M cell lines PCR analysis was employed. Cellular DNA was isolated and 40 $\mu$g was cleaved with the restriction enzyme BamHI. DNA samples were electrophoresed on a 1% agarose gel overnight and the approximate 1.8 kb fragment was isolated from the gel. This DNA fragment was extracted with phenol:ethanol and precipitated in ethanol. A total of 5 $\mu$g of DNA was used as the PCR template. The primers employed to identify the unique Krev-1 regions (from nucleotide 556 and nucleotide 840) were: 5'TATTC-TATTACAGCTCAGTCCACG3' (Seq. ID No. 1) and 5'AGGCTTCTTCTTTTCCACTGGTGT3' (Seq. ID No. 2). DNA samples were PCR amplified (34 cycles: 1 minute, 94° C., 1 minute, 60° C., 1 minute, 70° C.) after addition of the appropriate Krev-1 region primers. The predicted 285 nt fragment was detected after electrophoresis in a 1% agarose gel and ethidium bromide staining.

DNA and RNA Analysis

High-molecular-weight DNA was isolated from the transformed CREF cell lines as described (15). The presence of viral DNA sequences in these DNA samples was determined by DNA filter hybridization analysis as described (15, 24). Total cytoplasmic RNA was isolated from cells using the guanidinium-thiocyanate/cesium chloride method as described by Chirgwin et al. (27) Steady-state levels of the Ad5 E1A, Ad5 E1B, v-raf and v-src mRNAs were determined by Northern blot analysis of total-cytoplasmic RNA hybridized with appropriate random-primed $^{32}$P-labeled probes (28). Northern blots were also probed with a $^{32}$P-labeled GAPDH gene (29) to verify similar mRNA expression in the various cell types. Presence of HPV-18 and HPV-51 E6 gene expression in appropriate transformed CREF cells was determined by reverse transcription-polymerase chain reaction (RT-PCR) as described by Abdollahi et al. (30). Total cytoplasmic RNA was treated with 0.5 units DNase (Boehringer-Mannheim Biochemicals)/$\mu$g RNA in 15% glycerol—10 mM Tris, pH 7.5—2.5 mM MgCl$_2$—0.1 mM EDTA—80 mM KCl—1 mM CaCl$_2$ and 1 unit/ml RNasin (Promega®) at 30° C. for 10 minutes. RNA was extracted with phenol-chloroform, precipitated with sodium acetate/ethanol and RNA pellets were resuspended in diethylpyrocarbonate-treated H$_2$O. One $\mu$g of total RNA was reverse transcribed with 200 units of murine leukemia virus reverse transcriptase (Bethesda Research Laboratories) in 20 $\mu$l containing 1 mM deoxyribonucleotide triphosphates—4 mM MgCl$_2$—10 mM Tris, pH 8.3—50 mM KCl—0.001% gelatin, and 0.2 $\mu$g oligo-dT primer. Samples were diluted to 100 $\mu$l with buffer containing 0.2 mM deoxyribonucleotide triphosphates. 2 MM MgCl$_2$10 mM Tris, pH 8.3, 50 mM KCl and 0.001% gelatin. Fifty pmol of each primer, 1.5 units Taq DNA polymerase (Perkin-Elmer Cetus) were added and samples were covered with mineral oil, heated at 95° C. for 5 minutes and subjected to 20 cycles of PCR in a Perkin-Elmer Thermal Cycler using 2 minutes denaturation at 95° C., 1 minute annealing at 55° C. and 4 minutes polymerization at 72° C. After extraction with chloroform, 20 Ag of products were electrophoresed, blotted onto nylon filters and hybridized with an HPV-18 E6- or HPV-51 E6-specific probe. The template primers for HPV-18 E6 were 5'CTGCGTCGTTG-GAGTCTTTCC3' (Seq. ID No. 3) and 5'TTTGAGGATC-CAACACGGCGA3' (Seq. ID No. 4) (20) and the template primers for HPV-51 were 5'GGGAATTCCTTCACAGTC-CATCGCCGTTG3' (Seq. ID No. 5) and 5'GGGGGATC-CAACACCATGTTCGAAGACAAG3' (Seq. ID No. 6) (21).

Figure 1A:
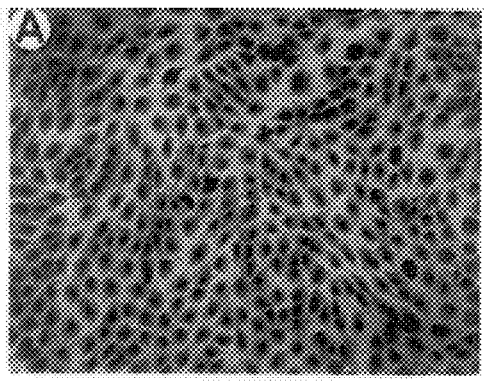
FIGS. 1A, 1B, 1C and 1D illustrate the morphology of CREF (A), Ha-ras- transformed CREF (B) and Ha-ras plus Krev-1-transformed CREF clones HK B1 (C) and HK B2 (D). Monolayer cultures were fixed in formaldehyde and stained with Giemsa at approximately×120.
Figure 1B:
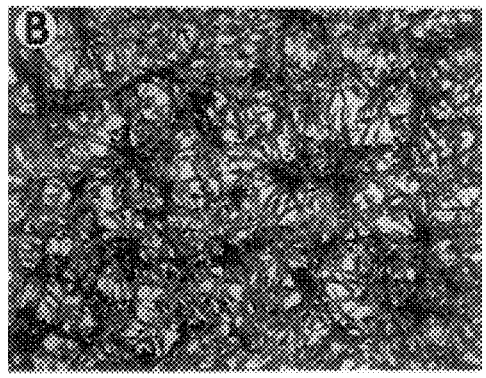
Figure 1C:
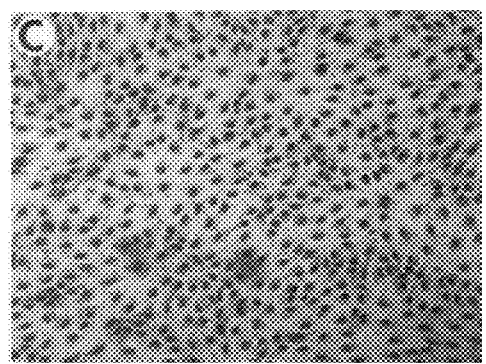
Figure 1D:
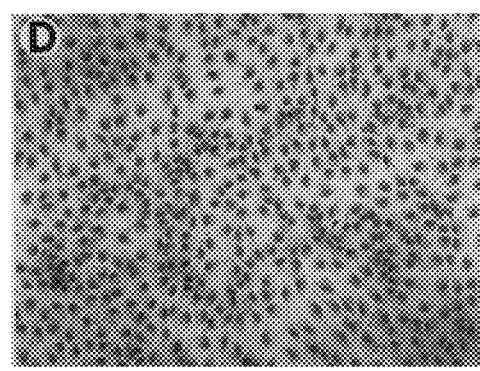
Figure 2A:
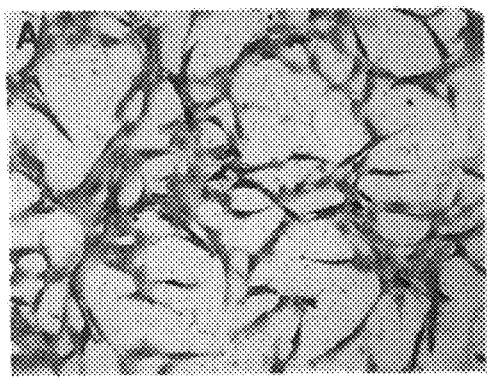
FIGS. 2A, 2B, 2C, and 2D, illustrate the morphology of H5hr1-transformed CREF (A2) (A), a human fibroblast cDNA-induced morphological revertant H5hr1-transformed A2 CREF clone (A2/Hu-Rev/cl 5) (B), v-src-transformed CREF (v-src/cl 1) (C) and a flat v-src revertant CREF clone (v-src/A2-Hu-Rev/cl 3) (D). Monolayer cultures were fixed in formaldehyde and stained with Giemsa at approximately× 120.
Figure 2B:
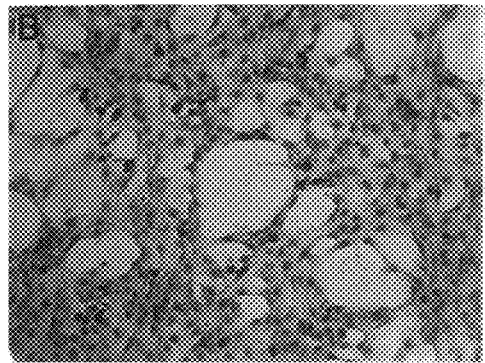
Figure 2C:
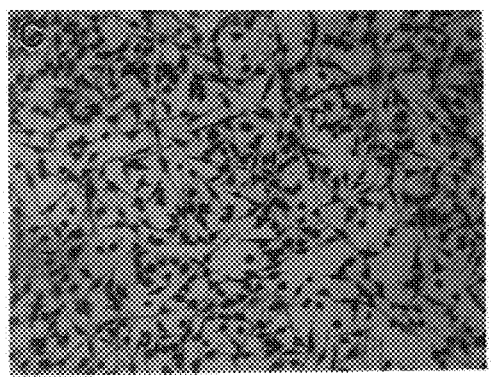
Figure 2D:
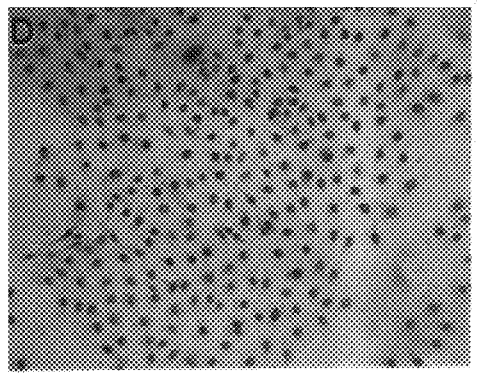
Figure 3:
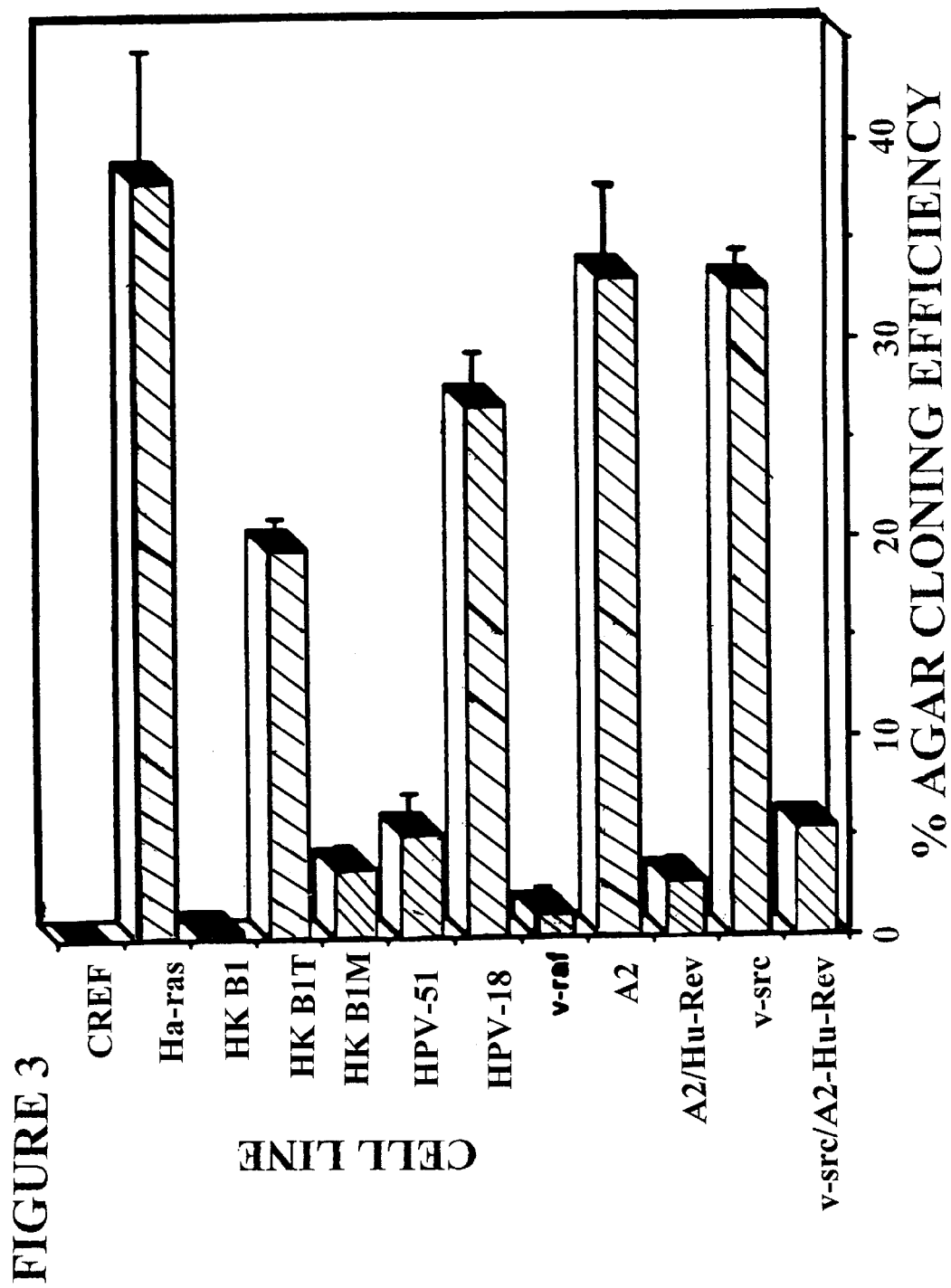
FIG. 3 illustrates the anchorage-independent growth of CREF and CREF cells transformed by diverse oncogenes and transformation-suppressor genes. Agar cloning efficiency (mean±S.D.) for triplicate samples inoculated at different cell densities was determined as previously described (15). Replicate studies of agar growth varied by ≦15%.

CAPE Induces Growth Suppression/Toxicity in CREF Cells Transformed by Diverse-Acting Oncogenes CREF cells transformed by wild-type and mutant adenovirus type 5 (Ad5) are sensitive to CAPE-induced growth suppression and toxicity (6). To determine if this effect is unique to Ad5-induced transformation of CREF cells or represents a more general phenomenon associated with the transformed phenotype, CREF cells were transformed by a series of viral oncogenes, including v-raf, HPV-18, HPV-51, Ha-ras and v-src. Transformation by the various viral oncogenes resulted in morphological transformation (FIGS. 1A–1D and 2A–2D) and acquisition of anchorage-independence (FIG. 3).

Figure 4A:
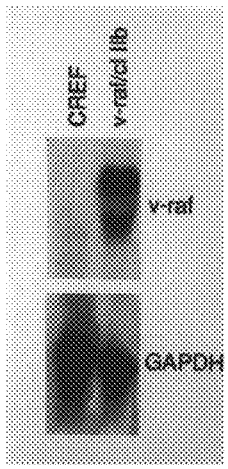
FIGS. 4A, 4B, and 4C illustrate the northern analysis of steady-state mRNA in CREF and viral oncogene-transformed CREF cells. A 20-$\mu$g aliquot of total cellular RNA was run on a 1.0% agarose gel and transferred to a nylon filter. Blots were hybridized with the indicated multiprime $^{32}$p-labeled gene probe. Filters were stripped and rehybridized with a multiprime $^{32}$P-labeled GAPDH probe. (A) Expression of v-raf and GAPDH mRNA in CREF and v-raf-transformed CREF (v-raf/cl IIb). (B) Expression of v-src and GAPDH mRNA in CREF, v-src-transformed CREF (v-src/cl 1) and flat revertant v-src-transformed CREF (v-src/A2 Hu-Rev/cl 3). (C) Expression of A5 E1A, A5 E1B and GAPDH mRNA in CREF, H5hr1-transformed CREF (A2) and flat revertant H5hr1-transformed CREF (A2/Hu-Rev/cl 5).
Figure 4B:
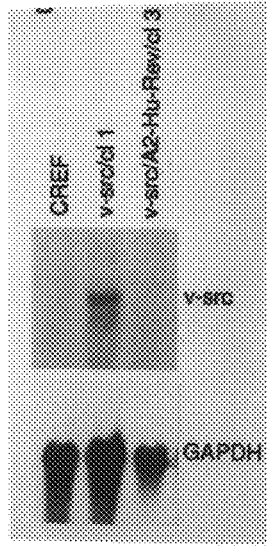
Figure 4C:
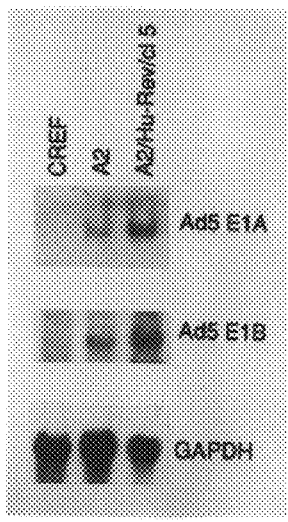
Figure 5A:
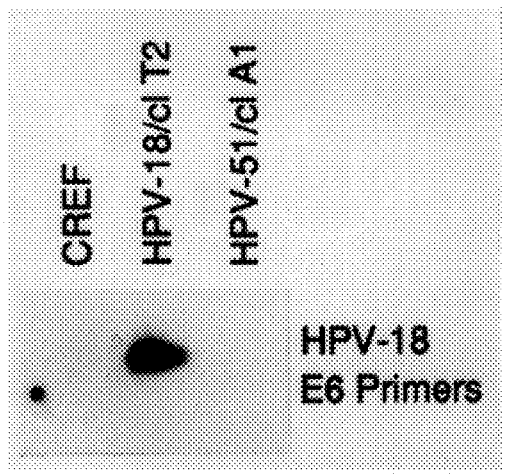
FIGS. 5A and 5B illustrate the expression of the HPV-18 and HPV-51 in CREF and HPV-18- and HPV-51-transformed CREF cells by RT-PCR. (A) Expression of HPV-18 in CREF, HPV-18-transformed CREF (HPV-18/cl T2) and HPV-51-transformed CREF (HPV-51/cl A1). (B) Expression of HPV-51 in CREF, HPV-18-transformed CREF (HPV-18/cl T2) and HPV-51-transformed CREF (HPV-51/cl A1). The specific E6 primers used for detecting HPV-18 and HPV-51 mRNA and the description of the RT-PCR procedure may be found in Materials and methods.
Figure 5B:
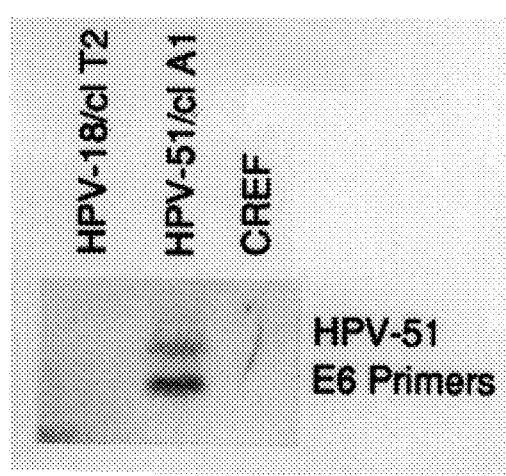
Figure 6A:
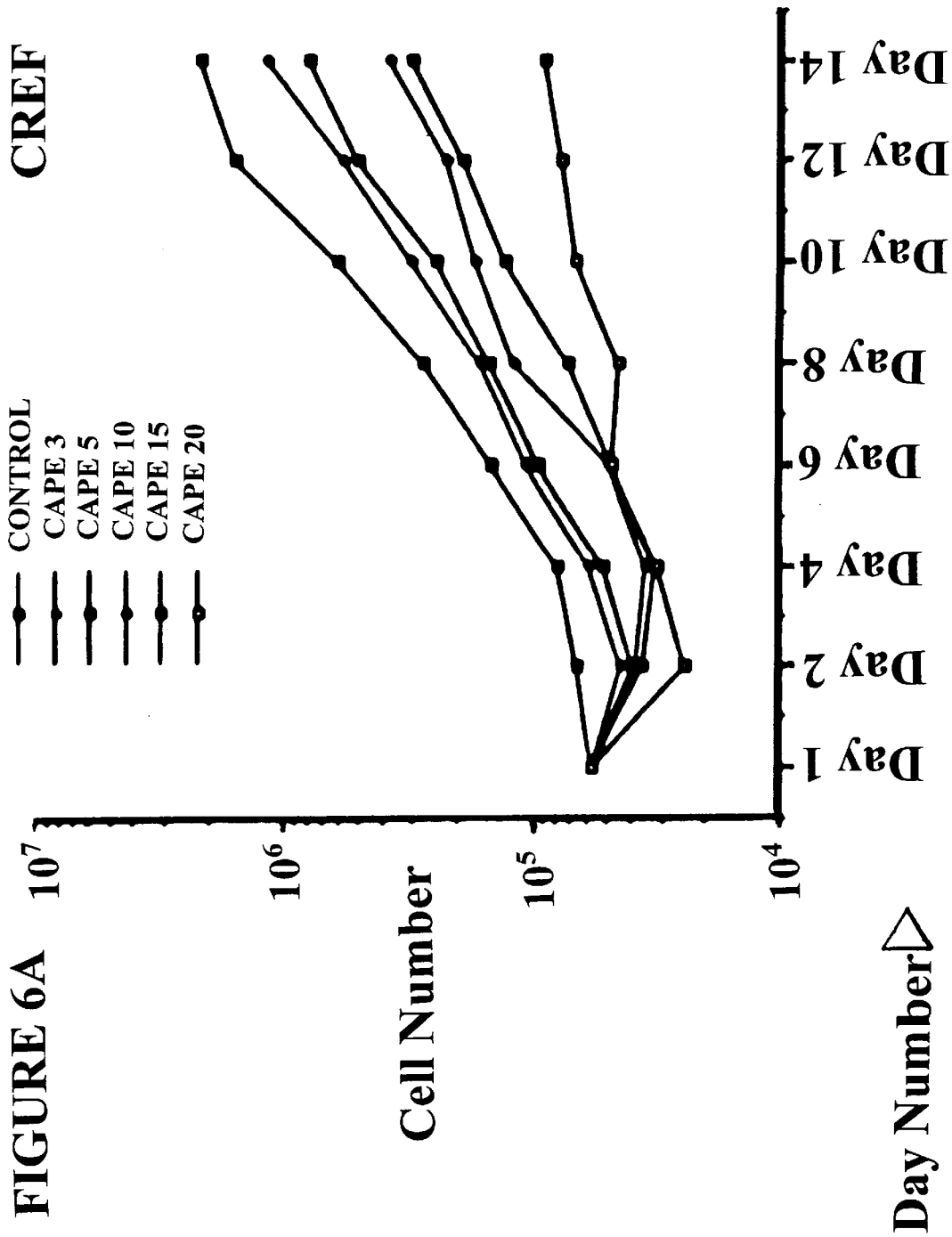
FIGS. 6A, 6B, 6C and 6D illustrate the effect of CAPE on the growth of (A) CREF, (B) v-raf-transformed CREF, (C) HPV-18-transformed and (D) HPV-51-transformed CREF. Cells were seeded at 2×10$^3$/3.5-cm plate, and approximately 16 hours later, the medium was changed and 0, 0.5, 1, 3, 5, 10 or 20 $\mu$g/ml CAPE added. Cell numbers from triplicate plates were determined at days 1, 2, 4, 6, 8, 10, 12 and 14.
Figure 6B:
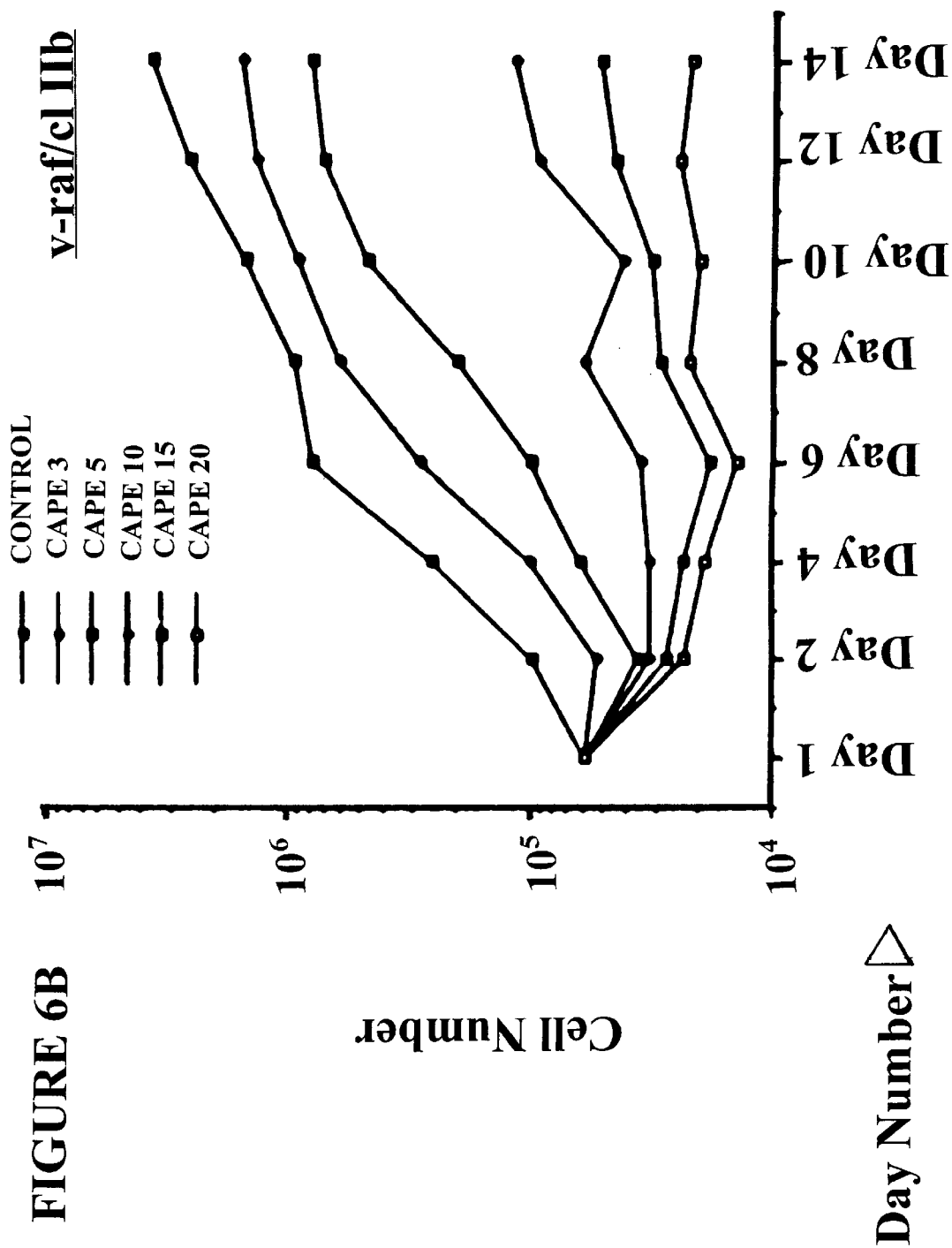
Figure 6C:
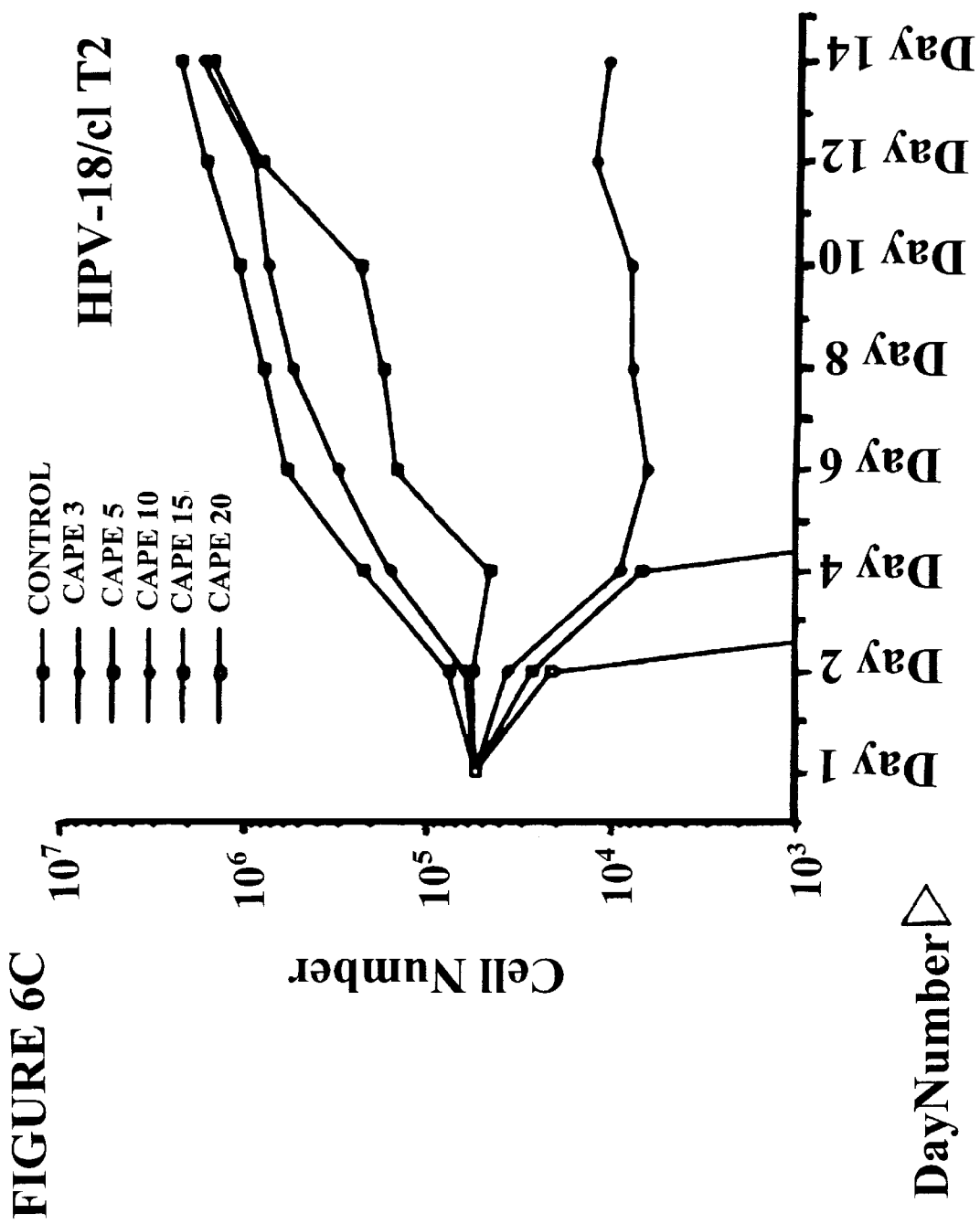
Figure 6D:
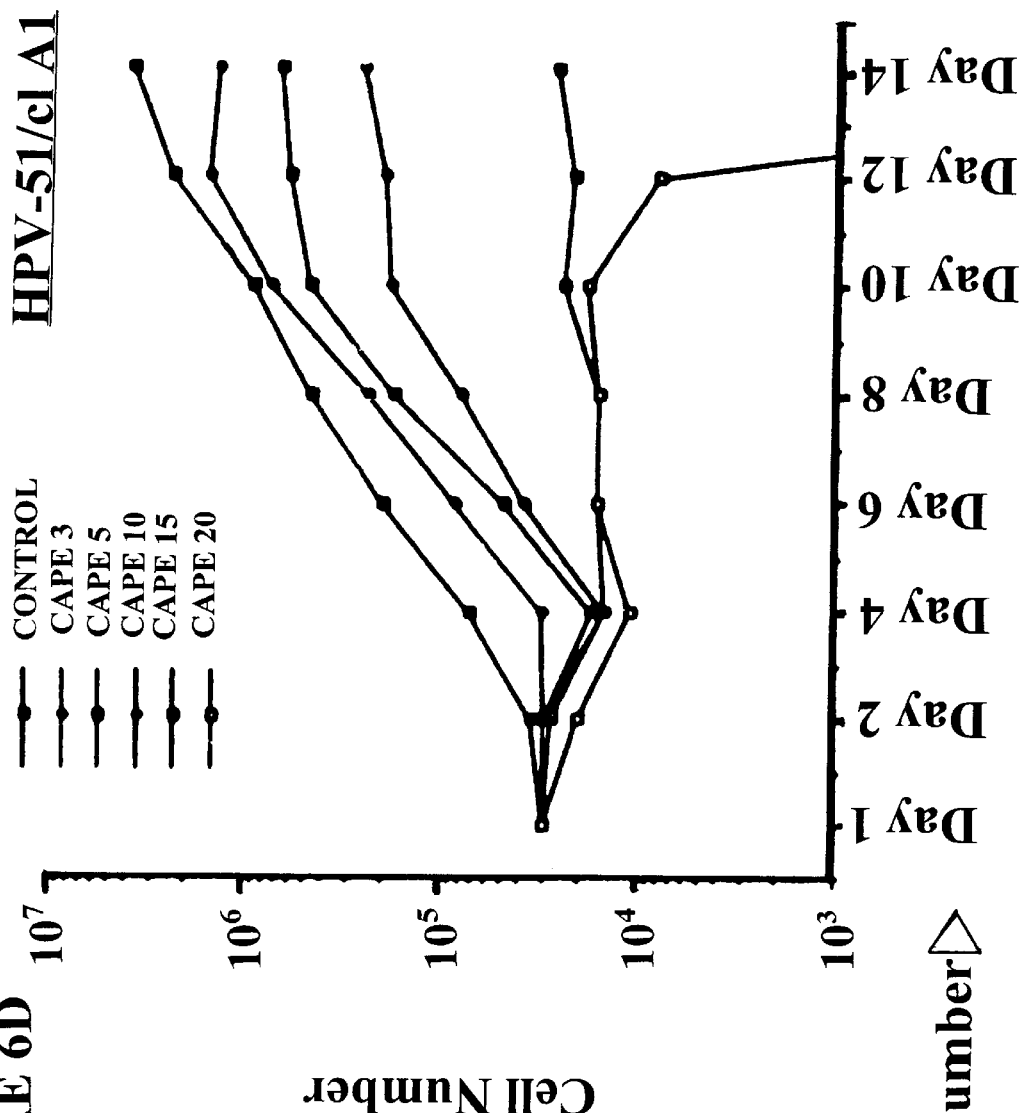

To ensure that CREF cells transformed by the different viral oncogenes express appropriate genetic information, Northern blotting was performed. CREF cells transformed by v-raf or v-src contained the appropriate viral mRNA (FIG. 4A and 4B). Similarly, previous studies have indicated that CREF cells transformed by Ha-ras (CREF-ras), CREF cells transformed by Ha-ras and cotransfected with Krev-1 (HK B1) and tumor-derived HK-B1 (HK B1-T) and metastasis-derived HK-B1 (HK B1-M) cells produce Ha-ras mRNA and elevated levels of the ras oncogene-encoded product, p21 (19). In addition, the H5hr1-transformed CREF clone, A2, reverted to a more contact-inhibited morphology (FIGS. 2A–2D) following a transfection with a human fibroblast expression vector cDNA library (A2/Hu-Rev/cl 5) continued to produce both A5 E1A and E1B mRNAs (FIG. 4C). Expression of the transformation related E6 mRNA in HPV-18- and HPV-51-transformed CREF cells was demonstrated by RT-PCR (FIGS. 5A and 5B). These observations indicate that the various cell lines used were transformed by the specific viral oncogene used and they express appropriate. viral oncogene-encoded genetic information.

The effect of CAPE on the growth of CREF and CREF cells transformed by v-raf, HPV-18 and HPV-51 is shown in FIGS. 6A–6D. In contrast to CREF cells, which display increases in cell number even when exposed to 15 $\mu$g/ml of CAPE, 10 $\mu$g/ml of CAPE is cytostatic toward v-raf/cl IIb and HPV-18/cl T2cells and 15 $\mu$g/ml of CAPE is cytostatic toward HPV-51/cl A1 cells. Twenty $\mu$g/ml of CAPE is cytotoxic toward HPV-18/cl T2and HPV-51/cl A1 cells. CREF cells transformed by Ha-ras or v-src are even more sensitive to the cytostatic and cytotoxic effects of CAPE. A dose of 3 $\mu$g/ml of CAPE is cytostatic toward Ha-ras and v-src cells, whereas 5 $\mu$g/ml or higher doses of CAPE are cytotoxic toward Ha-ras- and v-src-transformed CREF cells (FIGS. 7A–7D and FIG. 8). Similar patterns of CAPE sensitivity have also been observed using additional independently derived Ha-ras-and v-src-transformed CREF clones. These results indicate that CREF cells transformed by diverse acting oncogenes become sensitive to CAPE-induced growth suppression and cytoxicity. A direct correlation between the degree of CAPE sensitivity and expression of the transformed phenotype is also indicated, i.e., transformed cells displaying enhanced growth in agar are more sensitive to CAPE than cells displaying a lower efficiency of agar growth.

CAPE-induced Growth Suppression/Toxicity Correlates Directly with Expression of the Transformed Phenotype in Ha-ras-transformed CREF Cells The studies described above indicate that acquisition of the transformed phenotype by CREF cells, irrespective of the transforming viral oncogene used, results in an increase in sensitivity to CAPE-induced growth suppression. To determine if reversion of the transformed phenotype results in a change in sensitivity to CAPE, Ha-ras and Ha-ras/Krev-l expressing CREF cells (19) have been used (FIGS. 1B, 1C, 7A and 7B). CREF cells transformed by Ha-ras, Ha-ras/cl 5, are morphologically transformed, grow with approximately a 38% efficiency in agar and they induce both tumors and metastases in nude mice and syngeneic rats (FIGS. 1 and 3) (19). In contrast, CREF cells transformed by both Ha-ras and Krev-1 display a reversion in morphology to a more normal CREF-life phenotype, a reduction in anchorage independence and a suppression in tumorigenic and metastatic potential (19) (FIGS. 1 and 3). HK B1 cells do, however, induce both tumors (HK B1-T) and lung metastases (HK B1-M) in nude mice after a long latency period (19). Unlike HK BE parental cells, which display a similar pattern of gene expression as untransformed CREF cells, HK B1-T and specifically HK B1-M cells display a reversion in their gene expression to that of Ha-ras cells (19). HK B1-T and HK B1-M cells retain the original Krev-1 gene as indicated by PCR analysis (FIG. 9), continue to synthesize Krev-1 mRNA (19) and Ha-ras mRNA (19) and like HK B1 cells continue to synthesize the Ha-ras-encoded p21 protein (19). These results indicate that the Krev-1 gene can modify expression of the transformed state in Ha-ras cells at a post-transcriptional level. In this respect, this model is ideal for determining if CAPE-induced changes are related simply to the presence of the oncogene-encoded products or to the actual status of expression of the transformed phenotype.

Figure 7A:
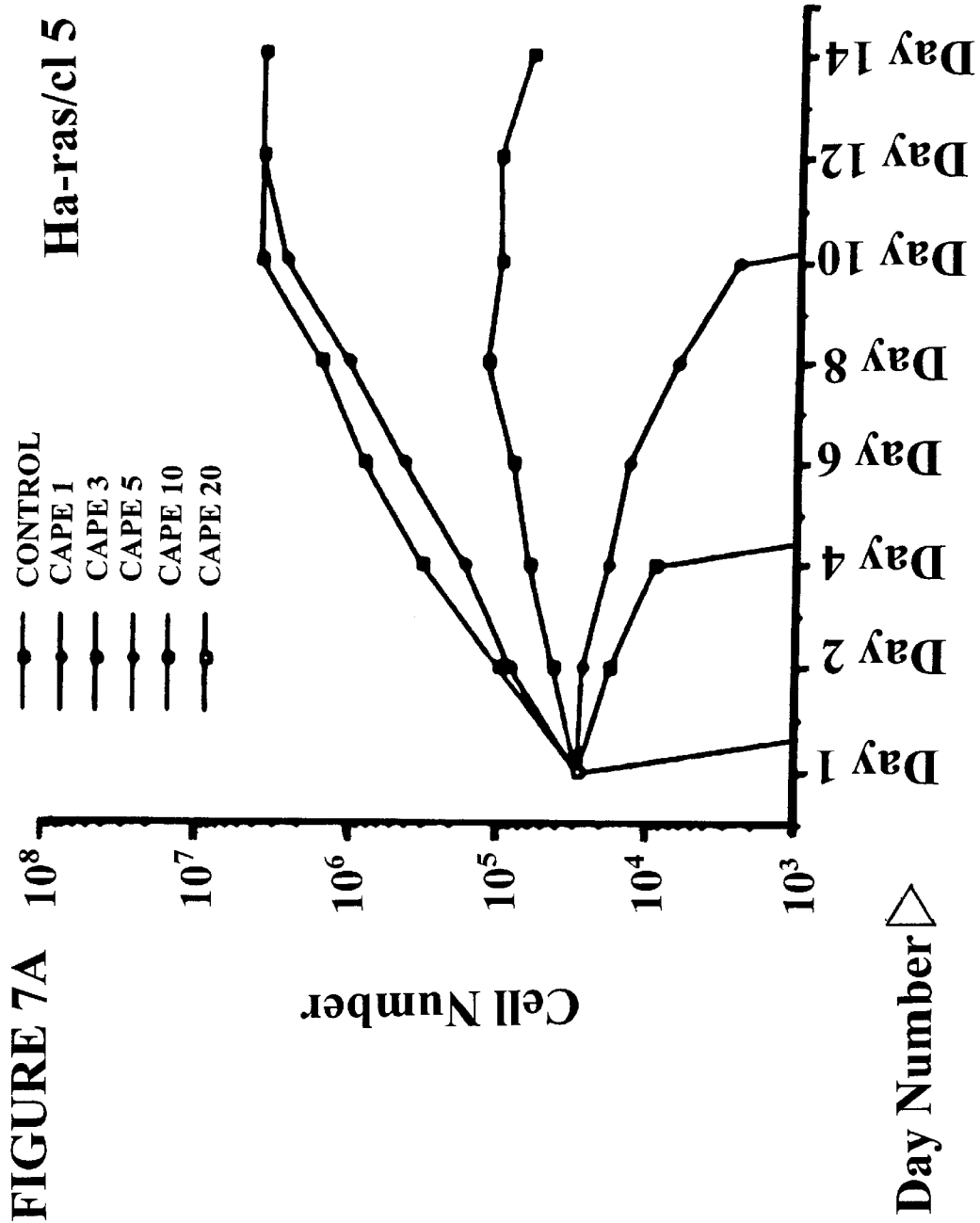
Figure 7B:
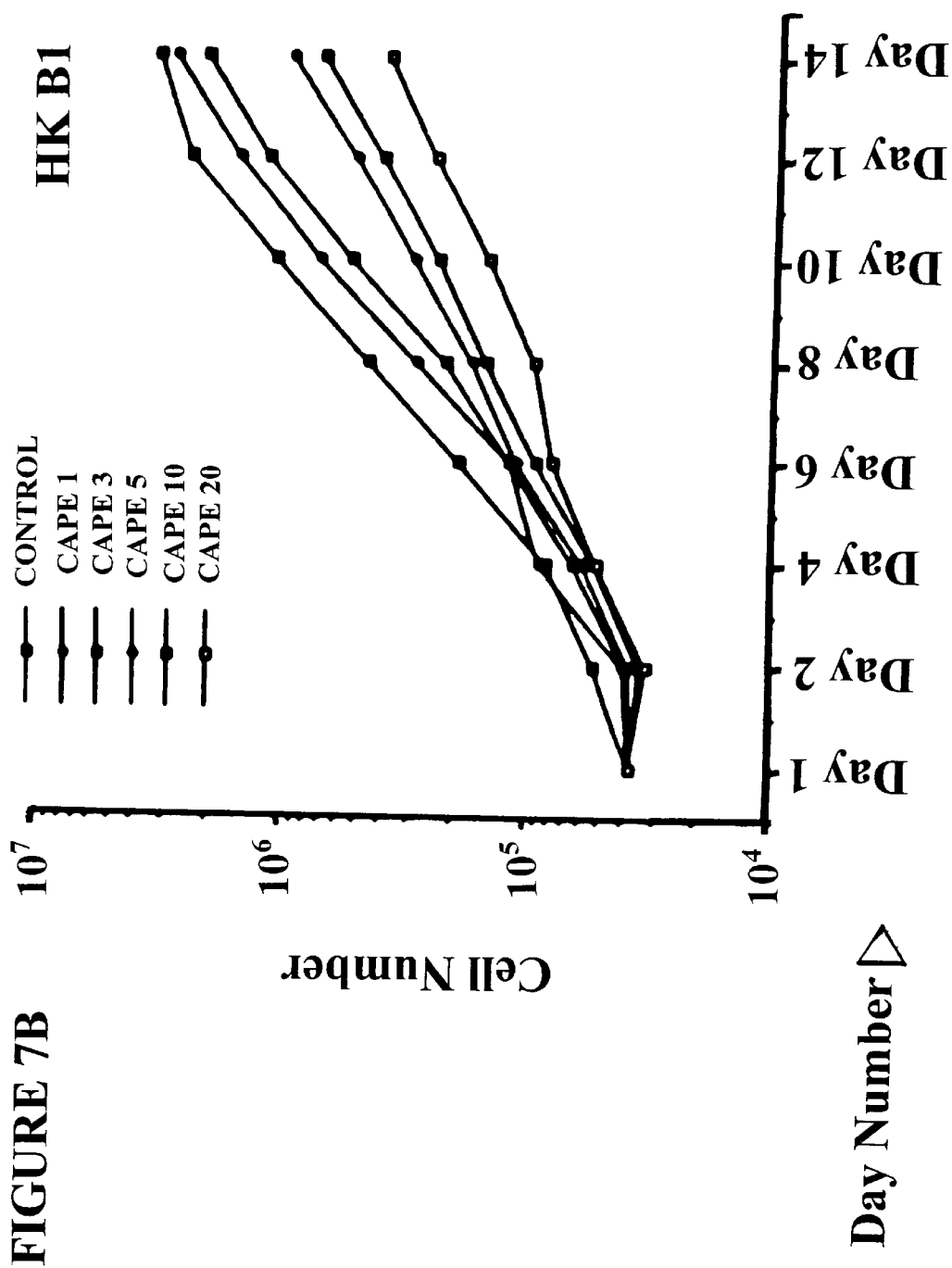
Figure 7D:
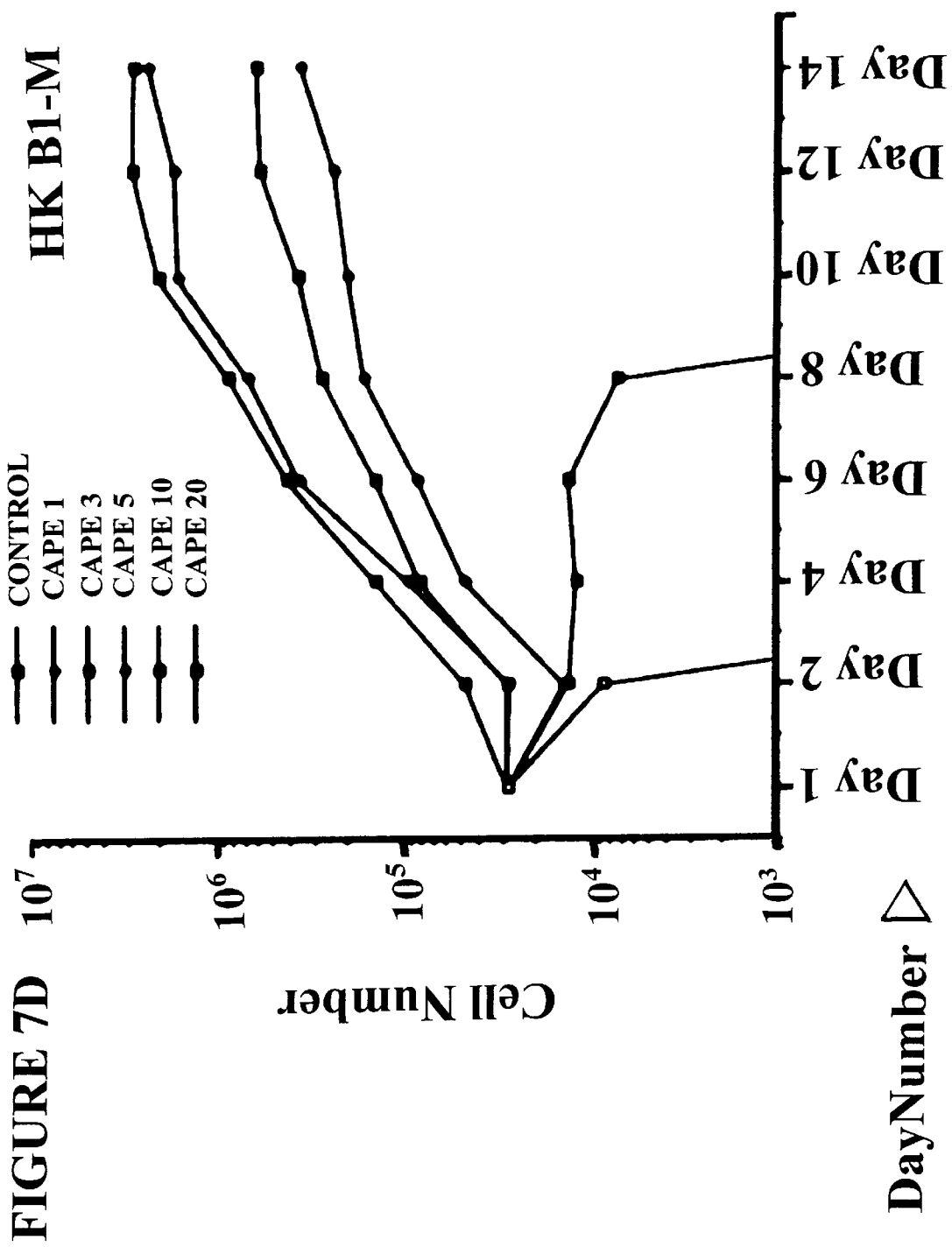
Figure 8A:
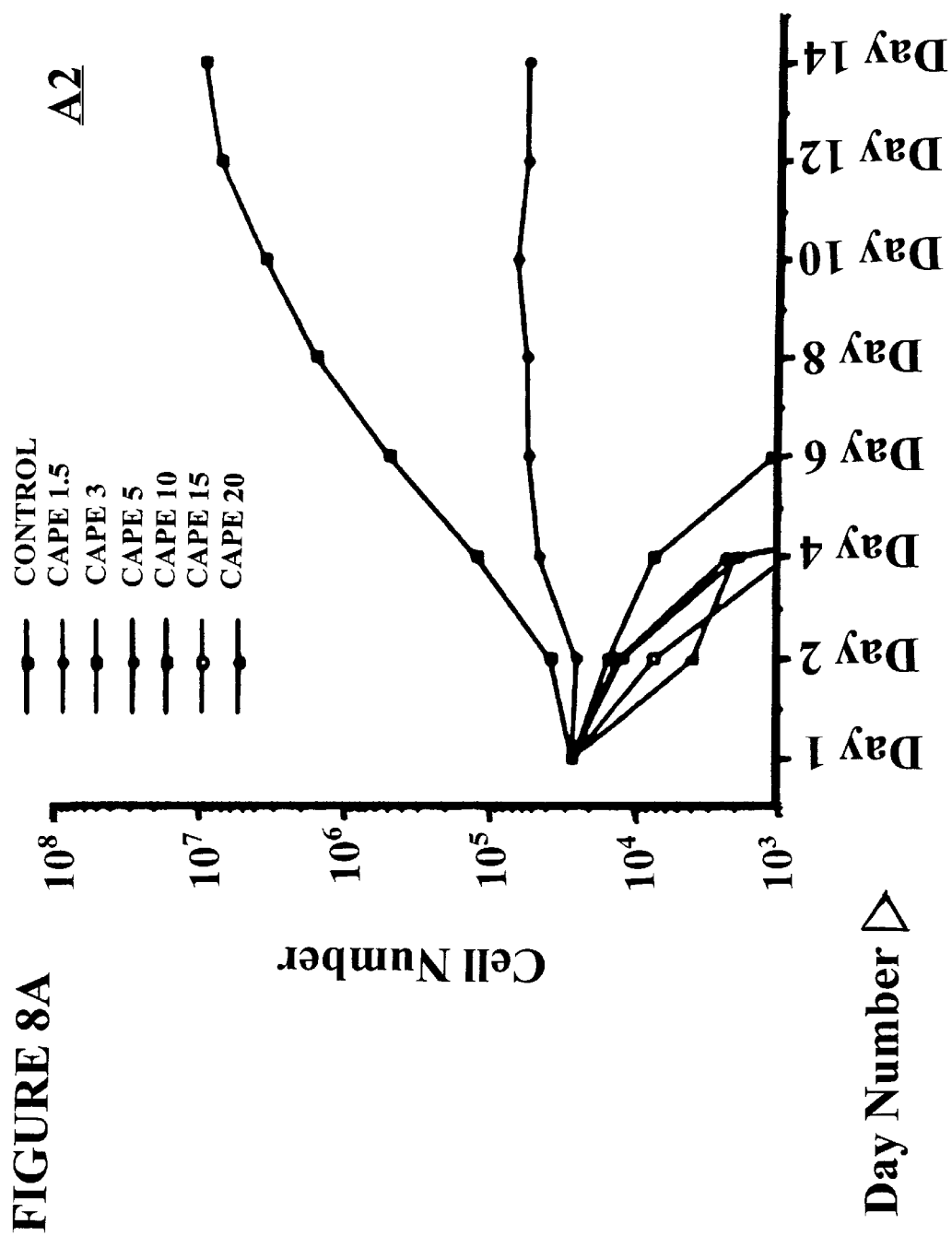
Figure 8B:
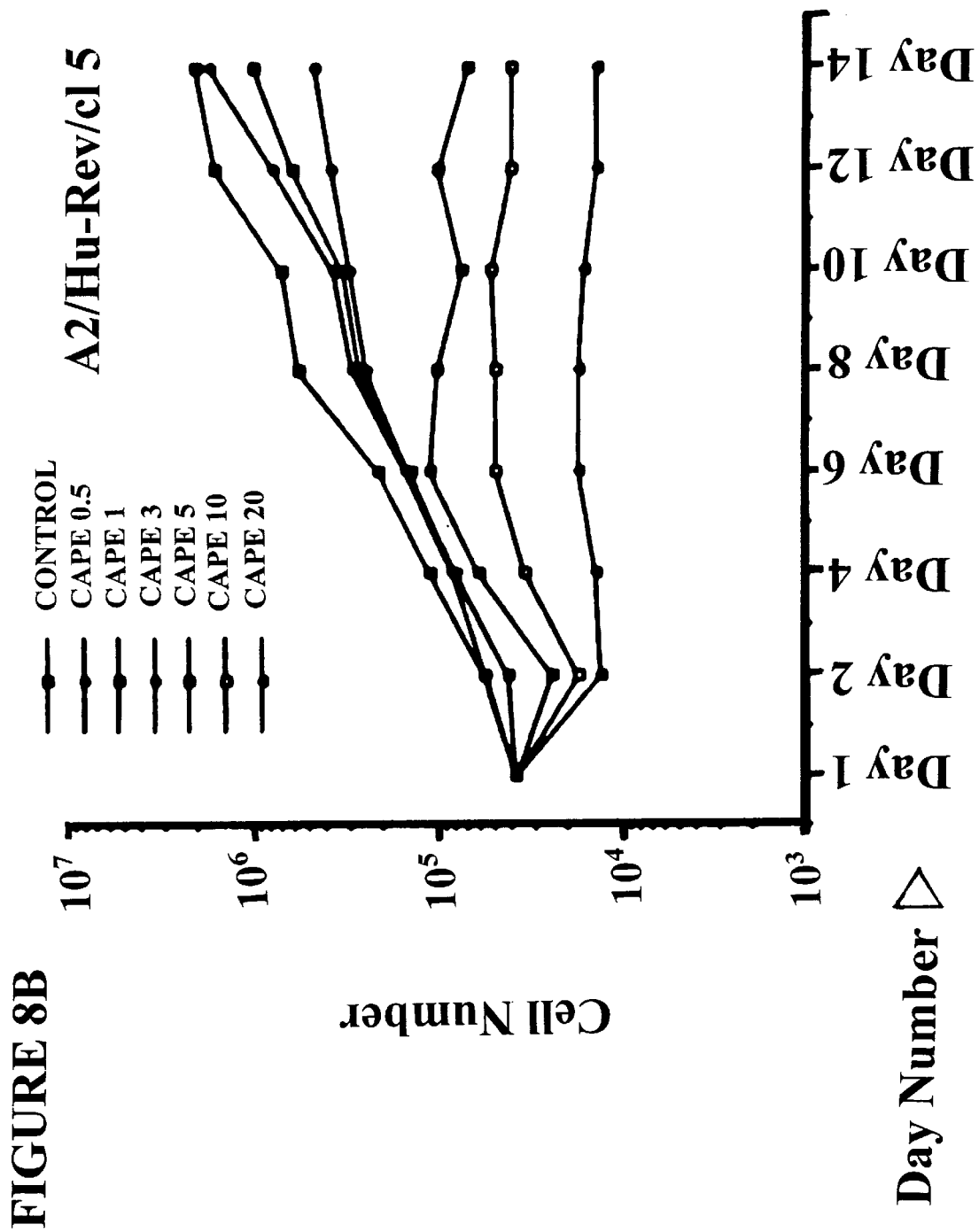
Figure 8C:
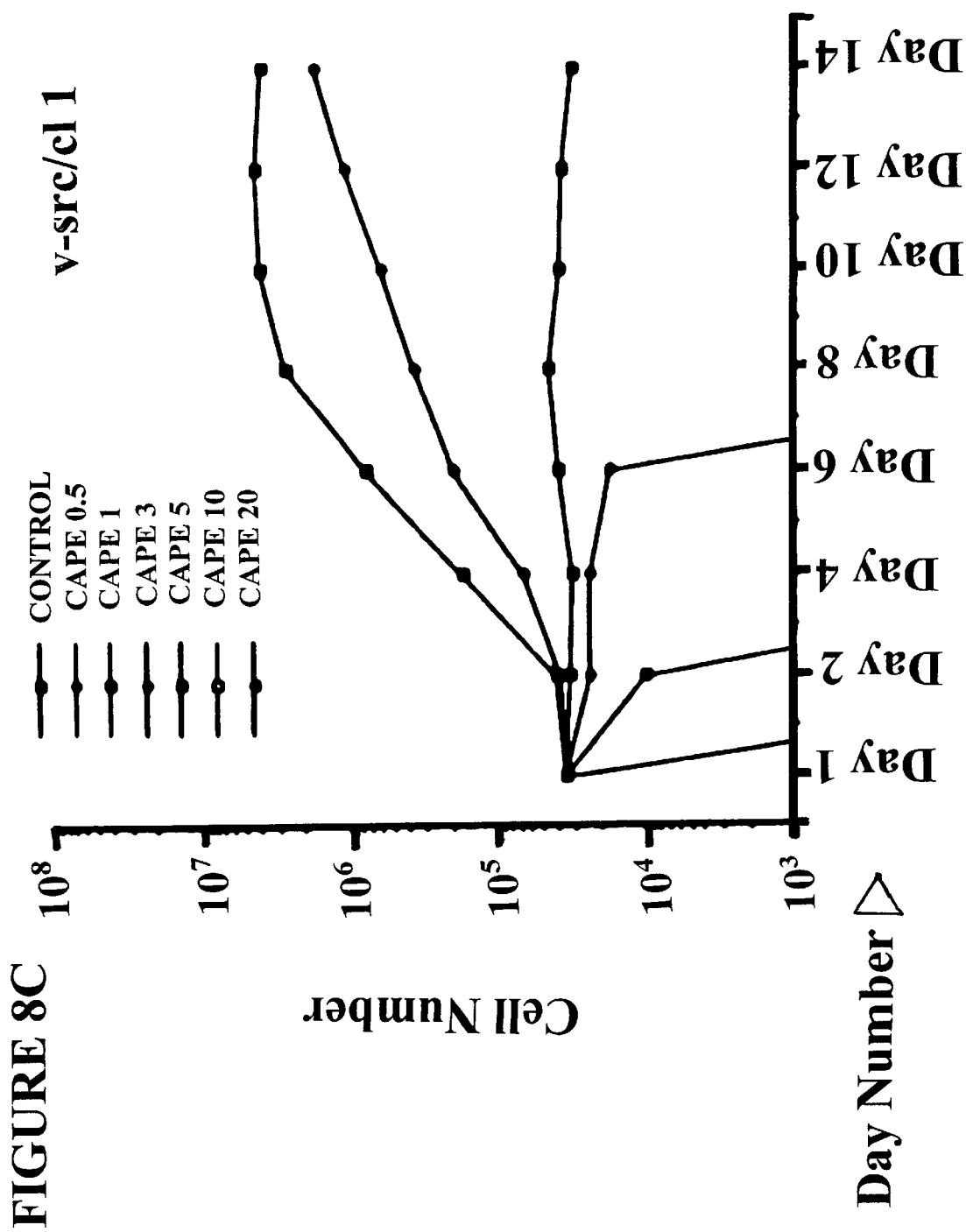
Figure 8D:
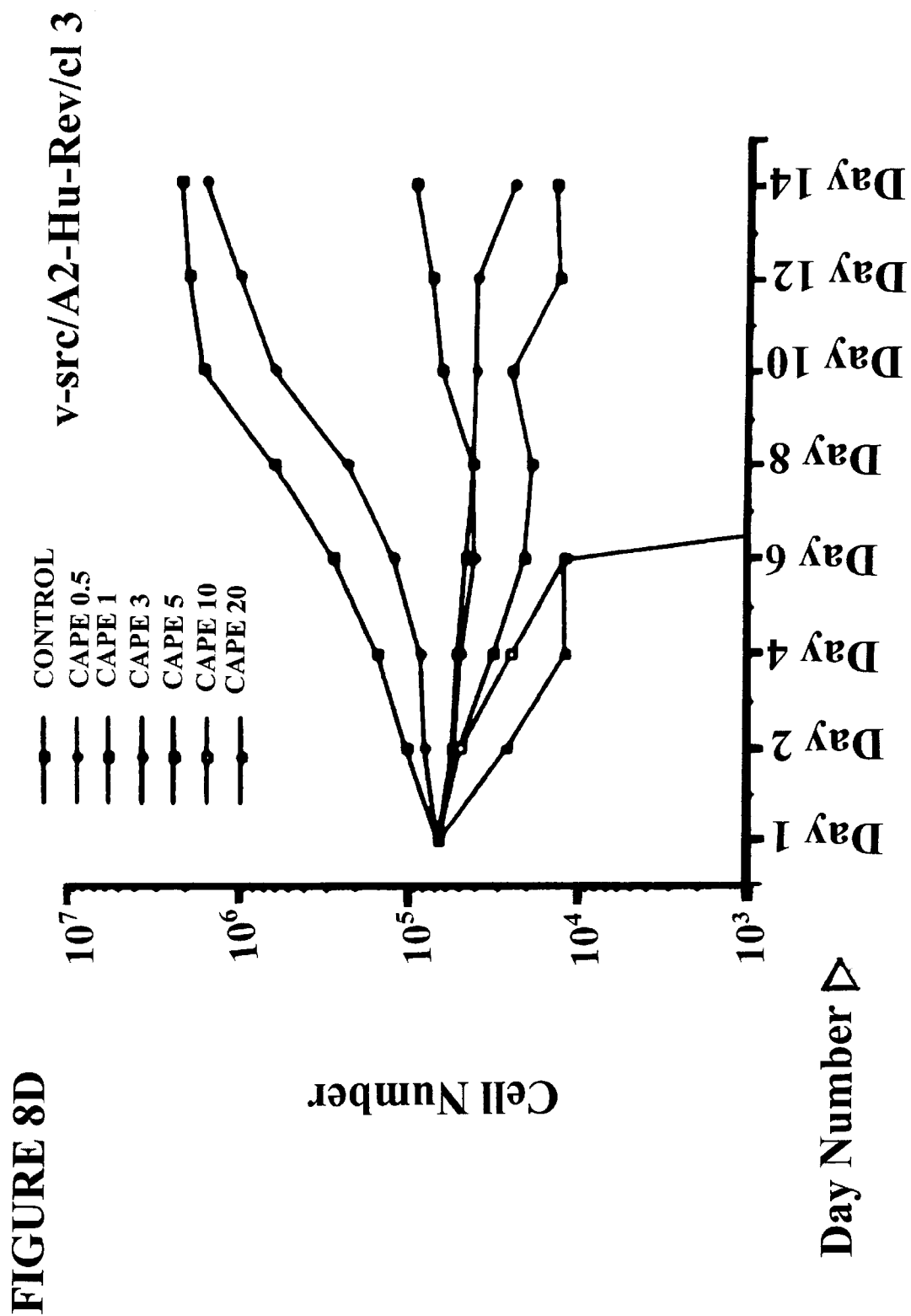

As shown in FIG. 7A, Ha-ras/cl 5cells are sensitive to both CAPE-induced growth suppression and cytotoxicity. In contrast, HK B1 cells, which display a CREF-like phenotype, acquire resistance to CAPE. In fact, even the highest dose of CAPE tested, 20 $\mu$g/ml, does not result in a loss of proliferative ability in HK B1 cells. A similar reversion to CAPE resistance is observed in two additional independent Ha-ras/Krev-1 clones, HK B2 and HK A3 (19). Escape from transformation-suppression following tumor- and metastasis-induction in nude mice results in HK B1-derived cells that have reacquired sensitivity to CAPE-induced growth suppression and cytotoxicity (FIG. 7B). HK B1-T and HK B1-M cells exhibit an increase in anchorage independence in comparison with HK B1 parental cells (FIG. 3) (19). HK B1-T cells also display an increase in anchorage-independence and they are more sensitive to CAPE than HK B1-M cells (FIGS. 3 and 7D). These results indicate that sensitivity to CAPE correlates directly with expression of the transformed state in CREF cells, as opposed to the mere presence of oncogene-encoded gene products.

CAPE-induced Growth Suppression/Toxicity Correlates Directly with Expression of the Transformed Phenotype in H5hr1- and v-src-transformed CREF Cells The studies described above using CREF cells transformed by Ha-ras and Ha-ras plus Krev-1 indicate a direct correlation between the transformed phenotype and CAPE sensitivity. For further investigation of this relationship, two transformation-revertant systems have been used. Using a modification of the strategy described by Kitayama et al. (11) which has resulted in the identification and isolation of the Krev-1 suppressor gene, an H5hr1-transformed CREF clone, A2, was transfected with an expression vector library containing cDNAs from normal human skin fibroblasts cloned into the pMAMneo vector. Cells were then selected in medium containing G418 and $10^{-7}$ M dexamethasone. A series of G418-resistant colonies, displaying a flat CREF-like morphology, was isolated and expanded for analysis. The A2 revertant clone, A2/Hu-Rev/cl 5were used. This revertant clone displays a CREF-like morphology, has an extended population doubling-time, grows with reduced efficiency in agar and has an increased latency time for tumor formation in nude mice (FIGS. 2 and 3). In contrast to these altered biological properties, both A2 and A2/Hu-Rev/cl 5cells express similar levels of Ad5 E1A and E1B MRNA (FIG. 4C). A2 cells are extremely sensitive to CAPE with 1.5 $\mu$g/ml resulting in growth suppression and 3 $\mu$g/ml or higher levels of CAPE inducing a cytotoxic effect (6) (FIG. 8). In contrast, although 5, 10 and 20 $\mu$g/ml of CAPE was cytostatic toward A2/Hu-Rev/cl 5 cells, no cytotoxic effect was apparent in the revertant cells.

The cDNA inducing reversion of the transformed phenotype in A2 cells was isolated and transfected into v-src-transformed CREF cells. Using a similar protocol as used in A2 transfections, a series of G418-resistant v-src-transformed CREF colonies displaying a reverted CREF-like morphology were isolated and expanded for further analysis (FIG. 2). The v-src-flat revertant, v-src/A2-Hu-Rev/cl 3 were used. In contrast to A2/Hu-Rev/cl 5cells that continue to express A5 gene products, vsrc/A2-Hu-Rev/cl 3 cells do not synthesize v-src MRNA that is detectable by Northern blotting (FIG. 4B). Southern blotting indicates that the v-src gene is still present in v-src/A2-Hu-Rev/cl 3 cells (FIG. 10). As observed with A2/Hu-Rev/cl 5versus A2 cells, v-src/A2-Hu-Rev/cl 3 cells display increased resistance to CAPE as compared to parental v-src cells (FIG. 8). These results provide compelling evidence indicating a direct correlation between expression of the transformed phenotype and CAPE sensitivity.

The ability of diverse acting cellular and viral oncogenes to induce transformation in primary and established rodent fibroblast cells indicates that transformation can proceed by different mechanisms (31–33). Irrespective of the transforming agent, transformed fibroblast cells often express similar cellular and biochemical changes (31, 32). Modifications i cellular phenotype associated with transformation of rodent fibroblasts often include decreased population doubling times, increased saturation densities, acquisition of anchorage-independence and tumorigenesis in athymic nude mice (31, 32). Compounds that display enhanced cytostatic/cytotoxic effects toward transformed versus normal cells represent potentially important agents for cancer therapy (34). It is demonstrated that CAPE displays a selective antiproliferative effect toward CREF cells transformed by viral oncogenes that display different modes of action, including Ads, v-raf, v-src, Ha-ras, HPV-18 and HPV-51. Evidence is also provided that both expression of the transformed phenotype and the degree of expression of transformation (measured by anchorage-independence) as opposed to simply the presence of the transforming oncogene product, are the mediators of CAPE sensitivity.

Previous studies have shown the effect of CAPE on growth and DNA synthesis in CREF cells infected, transfected or stably transformed by wild-type or mutant Ad5-transforming genes (6) has been analyzed in detail. CAPE inhibited, in a dose-dependent manner, both de novo and carcinogen-enhanced transformation of CREF cells by H5hrl. When transfected into CREF cells, a cold-sensitive Ads E1A gene only resulted in an inhibition in colony formation by CAPE when cells were grown at a permissive temperature for expression of the transformed phenotype, i.e., 37° C. CAPE was also most effective in inhibiting DNA synthesis in CREF cells containing either a wild-type Ads E1A gene (at 32 or 37° C.) or a cold-sensitive Ad5 E1A gene inducing a transformed phenotype (at 37° C.). A direct-requirement for a functional A5 E1A gene, capable of eliciting the transformed state, and CAPE sensitivity was demonstrated by using CREF cell stably transformed by a cold-sensitive A5 E1A gene or an A5 E1A gene under the transcriptional control of a mouse mammary tumor virus promoter. To determine the effect of the individual transforming proteins of the A5 A1A gene on CAPE sensitivity, CREF cells were stably transformed with cDNAs encoding either the 13S or the 12S E1A mRNA, which produce the 289 and 243 amino acid A5 transforming proteins respectively (6). Using these cell lines, it was demonstrated that CAPE was more growth suppressive toward cells expressing both transforming proteins followed by CREF cells transformed with the 13S cDNA and least effective against cells expressing only the 12S cDNA (6). It is demonstrated that CAPE-induced toxicity is eliminated when the H5hr1-transformed CREF clone, A2, is reverted to a more normal CREF-like phenotype by expression of a transfected human fibroblast cDNA. Revertant A2 clone, such as A2/Hu-Rev/cl 5, continue to express both the A5 E1A and E1B transforming genes. These results provide evidence that CAPE sensitivity in Ad5-transformed CREF cells is directly dependent on expression of the transformed state, as opposed to simply the presence of A5 E1A-transforming gene in A2/Hu-Rev/cl 5 cells.

The conclusion that CAPE-induced toxicity is a consequence of the extent of expression of the transformed phenotype is further supported by the following. Revertant of v-src transformed CREF cells, containing a human cDNA suppressor gene identified in A2/Hu-Rev/cl 5 cells, display a stable reversion in transformation-related properties and reacquire an increased resistance to CAPE-induced growth suppression and toxicity. The v-src revertant clone, v-src/A2-Hu-Rev/cl 3, no longer expresses v-src mRNA, indicating that the increased resistance to CAPE may be mediated by the absence of the transforming oncogene products. In the case of Krev-1-induced revertant of Ha-ras-transformed CREF cells, acquisition of a reverted transformation phenotype is not associated with changes in the levels of the Ha-ras oncogene products (19). Ha-ras cells are sensitive to CAPE-induced growth suppression and toxicity, whereas Krev-1 revertant Ha-ras transformed CREF clones, such as HK B1, are resistant to the cytostatic and cytotoxic effects of CAPE. When HK B1 cells escape transformation suppression, following long latency times in nude mice, tumors (HK B1-T) and lung metastases (HK B1-M) develop. The tumor- and lung metastasis-derived HK E1 clones coordinately display transformation-related properties and CAPE sensitivity. In addition, HK B1-T cells display a greater in vitro expression of anchorage-independence than the HK B1-M clones, and these cells are more sensitive to CAPE. These studies indicate a direct relationship between expression of the transformed state, with and without retention of the oncogene-encoded genetic information, and sensitivity to CAPE.

The mechanism by which CAPE induces its cytostatic and cytotoxic activity toward CREF cells transformed by diverse acting oncogenes is not presently known. In the case of Ad5 and human papilloma virus-induced transformation, common cellular genes may provide targets for oncoprotein interactions (35, 36). These include, an interaction between the Ad E1A- and HPV E7-encoded gene products and specific cellular proteins, such as the retinoblastoma gene product (p105-RB) and the p105-RB related proteins cyclin A (p107) and p130 (37).

Similarly, the Ads E1B - and HPV E6-encoded gene products specifically target the p53 tumor suppressor protein for inactivation (38). These observations have led to the hypothesis that induction of transformation by DNA viruses such as Ad and HPV may involve a direct inactivation of cellular gene products that normally function as suppressors of the transformed and oncogenic phenotype. In contrast, current evidence suggests that Ha-ras induced transformation is a consequence of the intrinsic guanosine triphosphatase activity of the oncogenic ras-encoded protein, p21, which functions as a component of the guanine nucleotide-binding protein signal transduction pathway in cells (39, 40). Similarly, the v-src gene encodes a membrane-associated tyrosine-specific kinase that is involved in cell signaling pathways and which may also involve small guanine nucleotide-binding proteins as target molecules (41). The transforming gene of murine sarcoma virus 3611, v-raf encodes a cytosolic serine/threonine kinase (22). The cellular homologue of v-raf, c-raf-1, is involved in regulating early gene expression changes associated with growth-factor stimulation of cells and acts downstream of ras (22, 42). Since all of the viral oncogenes described above render CREF cells sensitive to the antiproliferative effects of CAPE, apparently multiple and alternative biochemical changes that ultimately culminate in expression of the transformed state determine CAPE susceptibility. Furthermore, as indicated above the relative degree of CAPE-sensitivity is also directly related to expression of the transformed state, i.e., cells displaying greater anchorage-independence are more sensitive to CAPE-induced growth suppression and toxicity. Additional studies are necessary to define the common down-stream target that is shared by all of these oncogenes and which serves as the mediator of CAPE sensitivity. As a first step, it will be necessary to define the site within a cell in which CAPE initially interacts, i.e., the cell membrane, internal organelles, such as the mitochondria or the nucleus, specific enzymes, etc. Preliminary studies using [$^3$H]-labeled CAPE indicate no differential binding between CAPE-sensitive cells, such as A2, versus CAPE-resistant cells, such as CREF. These observations suggest that an intracellular target may prove to be the site of interaction with CAPE.

Elucidation of the biochemical changes that render a cell sensitive to CAPE-induced antiproliferative and cytotoxic activities could result in the identification of common cellular processes altered during oncogenic transformation. This information would prove beneficial in the rational design of chemotherapeutic agents that display antitumor activity toward cancer cells by exploiting common transformation endpoints as targets. In this context, appropriately designed agents would display selective activity toward neoplastic cells that developed as a consequence of the effects of diverse-acting oncogenes and/or the inactivation of diverse-acting tumor suppressor genes.

Second Series of Experiments

Inducible suppression cDNA cloning (IScClon) is a procedure for identifying and cloning growth inhibitory tumor suppressor genes. This approach can also be used to define genes controlling cellular differentiation and cell growth potential (senescence). IScClon is based on a hypothesis that constitutive expression of specific tumor suppressor genes in transformed and tumorigenic cell lines can result in a reversion in phenotype to a ore normal cellular state. In many contexts, this transformation-reversion may correlate with an irreversible loss in proliferative capacity, thereby, preventing the isolation of cells expressing novel tumor suppressor genes, IScClon permits the identification of cells containing tumor suppressor genes (based on a reversion in cellular morphology under conditions that induce tumor suppressor function) and allows growth of tumor suppressor gene containing cells (based on a return to a transformed state and/or resumption of growth under conditions that prevent tumor suppressor function). The IScClon approach should prove amenable to identifying and cloning genes mediating reversion of any transforming event, induced by either known or unidentified genetic changes.

Recent studies have focused on the application of IScClon for reverting the transformed phenotype of CREF cells transformed by human papilloma virus type 18 (HPV-18) (J. Lin, Z.-z, Su, D. Grunberger, S. G. Zimmer & P. B. Fiher, "Expression of sensitivity to growth phenotype induced by diverse acting viral oncogenes mediates sensitivity to growth suppressio induced by caffeine acid phenethyl ester (CAPE)", *Int. J. Oncology*, 5:5–15, 1994). CREF HPV-18/cl T2cells were transfected with a human fibroblast random 3'-primer or poly (dT) cDNA expression library cloned into a pMAM-neo vector (allowing inducible expression in the expression in the presence of dexamethasone (DEX)). When grown in the presence of G418, neomycin resistant-transformed CREF HPV-18/cl T2colonies developed. Application of DEX for 48 hours permitted the identification of colonies containing cells with a CREF-life morphology. Removal of DEX and further growth resulted in specific colonies that degenerated, remained morphologically normal or reverted back to the transformed phenotype. Both morphologically normal (constitutive in the absence of DEX) and inducible reverted (normal in the presence of DEX and transformed in the absence of DEX) colonies have been isolated and are being characterized.

Additional studies have been performed using the cold-sensitive host-range type 5 adenovirus mutant, H5hr1, transformed CREF clone, A2. A2 cells were transfected with a human fibroblast random 3'-primer or poly (dT) cDNA expression library cloned into a pMAM-neo vector (allowing inducible expression in the presence of dexamethasone (DEX)). Growth in the presence of G418 results in neomycin resistant-transformed A2 colonies. Addition of DEX for 48 hours permitted the identification of A2 colonies reverting to a more normal CREF-like morphology. As with HPV-18-transformed CREF cells, removal of DEX and further growth resulted in specific colonies that degenerated, remained morphologically normal or reverted back to the transformed phenotype. Both morphologically normal A2 (constitutive in the absence of DEX) and inducible reverted A2 (normal in the presence of DEX and transformed in the absence of DEX) colonies have been isolated and are being characterized.

The studies briefly described above suggest that both DEX-inducible and DEX-constitutive morphological revertant transformed cells will prove valuable in identifying genetic elements with the capacity to revert the transformed and oncogenic capacity of tumor cells. The modified IScClon strategy is shown in FIG. 12. The modified IScClon using antisense cDNAs shown in FIG. 13. The modified IScClon using tetracycline responsive promoters is shown in FIG. 14.

Construction of Random Unidirectional Linker-Primer, 3' Random Primer cDNA and Poly(dT) cDNA, Libraries from Normal Human Skin Fibroblast Cells For the inducible suppression cDNA cloning (IScClon) approach, both 3'-random primer and poly(dT) primer cDNA libraries are constructed from normal human skin fibroblast mRNA. The procedures are as described by Stratagene® and in detail in P. G., Reddy, Z.-z. Su and P. B. Fisher, "Identification and cloning of genes involved in progression of transformed phenotype", *Gene and Chromosome Analysis*, K. W. Adolph (Ed), Methods In Molecular Genetics, Vol. 1, Academic Press, San Diego, Calif., pp 68–102, 1993; and H. Jiang and P. B. Fisher, "Use of a sensitive and efficient subtraction hybridization protocol for the identification of genes differentially regulated during the induction of differentiation in human melanoma cells", *Mol. Cell. Different.*, 1(3):P285–299, 1993.

Total cellular RNA from normal human skin fibroblasts is isolated by the guanidinium isothiocyanate/CsCl centrifugation procedure and poly (A+) RNA was selected following oligo(dT) cellulose chromatography. A total of 10 μg of mRNA and 5 μg of random-primer (Stratagene, Cat. # 901151, Jun. 2, 1994 starts reverse transcription (3'-random primer cDNA library construction). Alternatively, a total of 5 μg of MRNA and 2.5 μg of a oligo(dT) primer (supplied in the Stratagene, ZAP-cDNA synthesis kit) starts reverse transcription (poly(dT) primer cDNA library construction). Protocols for constructing cDNA libraries are described by Stratagene and Reddy et al (1993) and Jiang and Fisher (1993).

Cloning of the 3'-Random Primer and Poly(dT) Primer cDNA Libraries into an Inducible Expression Vector (e.g. pMAMneo Vector Double-stranded phagemid DNAs (from λ ZAP) are prepared from the 3'-random primer and poly(dT) human fibroblast (HF) cDNA libraries using the mass excision procedure (Stratagene®) as described by Jiang and Fisher (1993). Briefly, $1 \times 10^7$ pfu of phagemids containing HF cDNA library are mixed with $2 \times 10^8$ SOLR strain of *Escherichia coli* and $2 \times 10^8$ pfu of ExAssist helper phage in 10 mM $MgSO_4$, followed by adsorption at 37° C. for 15 minutes. After the addition of 10 ml LB medium, the phagemid/bacteria mixture is incubated with shaking at 37° C. for 2 hours, followed by incubation at 70° C. for 15 minutes to heat inactivate the bacteria and the λ ZAP phage particles. After centrifugation at 4000 g for 15 minutes, the supernatant is transferred to a sterile polystyrene tube and stored at 4° C. before use.

To produce double-stranded DNA, $5 \times 10^7$ pfu of the phagemids is combined with $1 \times 10^9$ SOLR strain of *Escherichia coli*, which are nonpermissive for the growth of helper phage and therefore prevent coinfection by helper phage (Ref. 22 from Jiang and Fisher, 1993), in 10 mM $MgSO_4$, followed by adsorption at 37° C. for 15 minutes.

The phagemidslbacteria are transferred to 250 ml of LB medium containing 50 μg/ml ampicillin and incubated with shaking at 37° C. overnight. The bacteria are isolated by the alkali-lysis method (Ref. 18 from Jiang & Fisher, 1993) and purified through a QIAGEN-tip 500 column (QIAGEN Inc., Chatsworth, Calif.).

The purified double-stranded cDNA-containing phagemid is digested with the restriction endonucleases EcoRI and XhoI. The liberated cDNA inserts are isolated from the vector following digesting by electrophoresis in it agarose and electroelution. The purified cDNA inserts are ligated into the pMAMneo (Clontech) vector that has been incubated with the same restriction enzymes (EcoRI and XhoI) (inserts: vector=4:1). The ligated complex is then transfected into XL-1 blue strain of *Escherichia coli* resulting in the production of a dexamethasone (DEX)-inducible human fibroblast cDNA library. The production and purification of human fibroblast cDNA inserts/pMAMneo DNA is by the procedure developed by QIAGEN (QIAGEN plasmid Maxi protocol). The human fibroblast expression cDNA library (50 μl) in 500 ml LB medium with 50 μg/ml ampicillin overnight with shaking at 37° C. Plasmid DNA is isolated by the alkali-lysis method (Ref 18 from Jiang and Fisher, 1993) and purified through a QIAGEN-tip 500 column.

Identification of Cells Containing Growth and Tumor Suppressor Genes Using the Inducible Suppression cDNA Cloning (IScClon) Approach.

The IScClon approach is shown in FIG. 12. Approximately $1 \times 10^6$ target mammalian cells (CREF or CREF-Trans 6 cells containing transfected oncogenes (including, but not limited to Ad5, A5 mutant, v-src, HPV-18, Ha-ras) or high molecular weight (HMW) human tumor DNA; or human tumor cells) are transfected with 10 μg of plasmid HF cDNA library/pMAMneo DNA (HF cDNA library cloned in a sense orientation for transfer into CREF, CREF-Trans 6 or human tumor cells) by the calcium phosphate, lipofectin or electroporation technique. Transfected cells are replated 48 hr later and after 24 hr 300 μg/ml of G418 is added. After colonies form, approximately 7 to 21 days depending on the cell type, $10^{-6}$ M DEX is added. After 24 to 48 hr, plates are scanned microscopically and colonies displaying a morphologically reverted phenotype (to a normal morphology with sense inducible cDNAs) are identified and circled. DEX is then removed, colonies are isolated with metal cloning cylinders and maintained for further analysis as independent cell strains. These cell strains containing putative human growth suppressing and tumor suppressor genes can then be used to clone, sequence and characterize the potentially novel human tumor growth and transformation related tumor suppressor genes. At present, two types of cell strains have been identified: (a) cell clones that are reverted to a normal phenotype by treatment with DEX, but retain a normal cellular phenotype even in the absence of DEX; and (b) cell clones that display a reversible phenotype in the presence (normal phenotype) and absence (transformed phenotype) of DEX (see FIG. 12).

The IScClon approach using antisense cDNA constructs is shown in FIG. 13. Approximately $1 \times 10^6$ target normal human cells (skin fibroblast, epithelial, melanocyte, astrocyte, keratinocyte or other normal human cell type) are transfected with 10 μg of plasmid HF cDNA library/ mMAMneo DNA (HF cDNA library cloned in an antisense orientation) by the calcium phosphate, lipofectin or electroporation technique. Transfected cells are replated 48 hours later and after an additional 24 hours 300 to 500 μg/ml of G418 is added. Depending on the normal human cell type used transfected cells may be plated on feeder-layers consisting of irradiated CREF cells to improve colony forming efficiency. After colonies form, approximately 14 to 28 days depending on the cell type, $10^{-6}$M DEX is added. After 24 to 48 hours, plates are scanned microscopically and colonies displaying a morphologically reverted phenotype (to a transformed state) are identified and circled. Alternatively, colonies displaying growth under conditions limiting growth of the normal cell type, i.e., removal of specific growth factors, are also identified. DEX is then removed, colonies are isolated with metal cloning cylinders and maintained for further analysis as independent cell strains. Changes indicating potentially interesting antisense cDNAs include: changes in cellular morphology and growth properties (morphological transformation, anchorage-independence, acquisition of tumorigenic potential), ability to grow in the absence of specific growth factors (insulin, platelet derived growth factor TPA), loss of lineage-specific differentiation markers (melanin production, enzymatic changes, absence of cell surface antigenic markers) and unlimited growth potential (immortality and the loss of senescence). These cell strains containing putative human growth suppressing, tumor suppressing, differentiation suppressing and/or senescence suppressing genes can then be used to clone, sequence and characterize the potentially novel suppressor gene (see FIG. 12).

The IScClon approach using tetracycline (TET) suppressible tetracycline-responsive promoters is shown in FIG. 14. Approximately $1 \times 10^6$ target normal mammalian cells (CREF or CREf-Trans 6 cells containing transfected oncogenes (including, but not limited to, Ad5, Ad5 mutant, v-src, HPV-18, Ha-ras) or high molecular weight (HMW) human tumor DNA; or human tumor cells are transfected with 10 μg of plasmid PUHD15-1 and 1 μg of pSV2-neo DNA by the calcium phosphate, lipofectin or electroporation technique. Transfected cells are plated 48 hours later and after an additional 24 hr 300 to 500 μg/ml of G418 is added. G418 resistant colonies are identified after 7 to 21 days, isolated and cell strains expressing the tetracycline repressor fused to the activation domain of the herpes virus transcriptional activator, VP-16, are identified. These transformed cells are then transfected with 10 μg of plasmid pUHD10-3 containing the HF cDNA library and 1 μg of pRSV1.1 DNA is (containing a hygromycin resistance gene) by the calcium phosphate, lipofectin or electroporation technique. Transfected cells (grown in the presence of 1 μg/ml of tetracycline) are replated 48 hr later and after an additional 24 hr 100 to 400 μg/ml of hygromycin plus 1 μg/ml tetracycline is added. Hygromycin resistant colonies are identified 7 to 21 days later. Tetracycline is removed and after 48 hr, plates are scanned microscopically and colonies displaying a morphologically reverted normal cellular phenotype are identified and circled. Tetracycline (1 μg/ml) is then added, colonies are isolated with metal cloning cylinders and maintained for further analysis as independent cell strains. These cell strains containing putative human growth suppressing and tumor suppressor genes can then be used to clone, sequence and characterize the potentially novel human tumor growth and transformation related tumor suppressor gene (see FIG. 14).

References

1. Bishop, J. M., (1987) The molecular genetics of cancer. *Science* 235:305–311.
2. Weinberg, R. A., (1991) Tumor suppressor genes. *Science* 254:1138–1146.
3. Marshall, C. J., (1991) Tumor suppressor genes. *Cell* 64:313–326.
4. Levine, A. J. (1993) The tumor suppressor genes. *Annu. Rev. Biochem.* 62:623–651.
5. Grunburger, D., Banerjee, R., Eisinger, K., Oltz, E. M., Efros, M., Estevez, V. and Nakanishi, K., (1988) Preferential cytotoxicity on tumor cells of caffeine acid phenethyl ester isolated from propolis. *Experiential* 44:230–232.
6. Su, Z-z., Grunberger, D., and Fisher, P. B., (1991) Suppression of adenovirus type 5 E1A-mediated transformation and expression of the transformed phenotype by caffeine acid phenethyl ester (CAPE). *Mol. Carcinogen.* 4:231–242.
7. Rao, V. R., Desai, D., Kaul, B., Amin, S. and Reddy, B. S., (1992) Effect of caffeine acid esters on carcinogen-induced mutagenicity and human colon adenocarcinoma cell growth. *Chem-Biol. Interacts* 84:277–290.
8. Rao, V. R., Desai, D., Simi, B, Kulkarni, N., Amin, S. and Reddy, B. S., (1993) Inhibitory effect of caffeine acid esters on azoxymethane-induced biochemical changes and aberrant crypt foci formation in rat colon. *Cancer Res.* 53:4182–4188.
9. Frankel, K., Wei, H., Bhimani,R., Zadunaisky, J. A., Ferraro, T., Huang, M. T., Conney, A. H. and Grunberger, D., (1993) Inhibition of tumor promoter-mediated processes in mouse skin and bovine lens by caffeine acid phenethyl ester. *Cancer Res.* 53:1255–1261.
10. Guarini, L., Su, Z-z., Zucker, S., Lin, J., Grunberger, D. and Fisher, P. B., (1992) Growth inhibition and modulation of antigenic phenotype in human melanoma and glioblastoma multiforme cells by caffeine acid phenethyl ester (CAPE). *Cell Mol. Biol.* 38:513–527.
11. Kitayama, H., Sugimoto, Y., Matsuzaki, T., Ikawa, Y. and Noda, M., (1989) A ras-related gene with transformation suppressor activity. *Cell* 56:77–84.
12. Noda, M., Kitayama, H., Matsuzaki, T., Sugimoto, Y., Okayama, H., Bassin, R. H. and Ikawa, Y., (1989) Detection of genes with potential for suppressing the transformed phenotype associated with activated ras genes. *Proc. Natl. Acad. Sci., U.S.A.* 86:162–166.
13. Zhang, K., Noda, M., Vass, W. C., Papageorge, A. G. and Lowy, D. R., (1990) Identification of small clusters of divergent amino acids that mediate the opposing effects of ras and Krev-1. *Science* 249:162–165.
14. Fisher, P. B., Mufson, R. A., Weinstein, I. B. and Little, J. B., (1981) Epidermal growth factor, like tumor promoters, enhances viral and radiationinduced cell transformation. *Carcinogenesis* 2:183–187.
15. Fisher, P. B., Babiss, L. E., Weinstein, I. B. and Ginsberg, H. S., (1982) Analysis of type 5 adenovirus transformation with a cloned rat embryo cell line (CREF). *Proc. Natl. Acad. Sci., U.S.A.* 79:3527–3531.
16. Boylon, J. F., Jackson, J., Steiner, M., Shih, T. Y., Duigou, G. J., Roszman, T., Fisher, P. B. and Zimmer, S. G., (1990) Role of the Ha-ras (ras$^H$) oncogene in mediating progression of the tumor cell phenotype (review). *Anticancer Res.* 10:717–724.
17. Boylon, J. F., Shih, T. Y., Fisher, P. B. and Zimmer, S. G., (1992) Induction and progression of the transformed phenotype in cloned rat embryo fibroblast cells: studies employing type 5 adenovirus and wild-type and mutant Ha-ras oncogenes. *Mol. CarcinoQenesis* 5:118–128.
18. Su, Z-z., Zhang, P. and Fisher, P. B., (1990) Enhancement of virus and oncogene-mediated transformation of cloned rat embryo fibroblast cells by 3-aminobenzamide. *Mol. Carcinogenesis* 3:309–318.
19. Su, Z-z., Austin, V. N., Zimmer, S. G. and Fisher, P. B., (1993) Defining the critical gene expression changes associated with expression and suppression of the tumorigenic and metastatic phenotype in Ha-ras-transformed cloned rat embryo fibroblast cells. *Oncogene* 8:1211–1219.
20. Schneider-Gadicke, A. and Schwarz, E., (1986) Different human cervical carcinoma cell lines show similar transcription patterns of human papillomavirus type 18 early genes. *EMBO J.* 5:2285–2292.
21. Lungu, O., Crum, C. P. and Silverstein, S., (1991) Biologic properties and nucleotide sequence analysis of human papillomavirus type 51. *J. Virol.*, 65:4216–4225.
22. Rapp, U. R., Goldsborough, M. D., Mark, G. E., Bonner, T. I., Groffen, J., Reynolds, F. H., Jr., and Stephenson, J. R., (1983) Structure and biological activity of v-raf, a unique oncogene transduced by a retrovirus. *Proc. Natl. Acad. Sci., U.S.A.*, 80:4218–4222.
23. Jove, R. and Hanafusa, H., (1987) Cell transformation by the viral src oncogenes. *Annu. Rev. Cell Biol.* 3:31–56.
24. Babiss, L. E., Ginsberg, H. S. and Fisher, P. B., (1983) Cold-sensitive expression of transformation by a host range mutant of type 5 adenovirus. *Proc. Natl. Acad. Sci. U.S.A.*, 80:1352–1356.
25. Babiss, L. E., Liaw, W-S., Zimmer, S. G., Godman, G. C., Ginsberg, H. S. and Fisher, P. B. (1986) Mutations in the E1a gene of adenovirus type 5 alter the tumorigenic properties of transformed cloned rat embryo fibroblast cells. *Proc. Natl. Acad. Sci., U.S.A.* 83:2167–2171.
26. Su, Z-z., Leon, J. A., Jiang, H., Austin, V. N., Zimmer, S. G. and Fisher, P. B., (1993) Wild-type adenovirus type 5 transforming genes function as transdominant suppressors of oncogenesis in mutant adenovirus type 5 transformed rat embryo fibroblast cells. *Cancer Res.* 53:1929–1938.
27. Chirgwin, J. M., Przbyla, A. E., MacDonald, R. J. and Rutter, W. J., (1979) Isolation of biologically active ribonucleic acid from sources enriched in ribonuclease. *Biochemistry* 18:5294–5299.
28. Babiss, L. E., Young, C. S. H., Fisher, P. B. and Ginsberg, H. S., (1983) Expression of adenovirus E1A and E1B gene products and the *Escherichia coli* HGPRT gene in KB cells. *J. Virol.* 46:454–465.
29. Jiang, H., Su, Z-z., Datta, S., Guarini, L., Waxman, S. and Fisher, P. B., (1992) Fludarabine phosphate selectively inhibits growth and modifies the antigenic phenotype of human glioblastoma multiforme cells expressing a multidrug resistance phenotype. *Int. J. Oncol.* 1:227–239.
30. Abdollabi, A., Lord, K. A., Hoffman-Liebermann, B. and Liebermann, D. A., (1991) Interferon regulatory factor 1 is a myeloid differentiation primary response gene induced by interleukin-6 and leukemia inhibitory factor: role in growth inhibition. *Cell Growth Different.* 2:401–407.
31. Fisher, P. B., (1984) Enhancement of viral transformation and expression of the transformed phenotype by tumor promoters. In: *Tumor Promotion and Cocarcinogenesis In Vitro, Mechanisms of Tumor Promotion.* T. J. Slaga (ed)., Florida, CRC Press, pp. 57–123.
32. Bishop, J. M., (1991) Molecular themes in oncogenesis. *Cell* 64:235–248.
33. Liotta, L. A., Steeg, P. S. and Stetler-Stevenson, W. G., (1991) Cancer Metastasis and angiogenesis: an imbalance of positive and negative regulation. *Cell* 64:327–336.
34. Fisher, P. B., and Rowley, P. T., (1991) Regulation of growth, differentiation and antigen expression in human tumor cells by recombinant cytokines: Applications for the differentiation therapy of human cancer. In: *The Status of Differentiation Therapy of Cancer.* S. Waxman, G. B. Rossi and F. Takaku (eds)., New York, Raven Press, pp. 201–213.
35. Vousden, K., (1993) Interactions of human papillomavirus transforming proteins with the products of tumor suppressor genes. *FASEB J.* 7:872–879.
36. Moran, B., (1993) Interaction of adenoviral proteins with pRB and p53. *FASEB J.* 7:880–885.
37. Dyson, N., and Harlow, E., (1992) Adenovirus E1A targets key regulators of cell proliferation. *Cancer Surv.* 12:161–195.
38. Levine, A. J., (1990) The p53 protein and its interactions with the oncogene products of the small DNA tumor viruses. *Virology*, 177:419–426.
39. Lowy, D. R. and Willumsen, B. M., (1993) Function and regulation of ras. *Annu. Rev. Biochem.* 62:851–891.
40. Noda, M., (1992) Mechanisms of reversion. *FASEB J.* 7:834–846.
41. Pawson, T. and Gish, G. D., (1992) SH2 and SH3 domains: from structure to function. *Cell* 71:359–362.
42. Kolch, W., Heidecker, G., Lloyd, P. and Rapp, U. R., (1991) Raf-1 protein kinase is required for growth of induced NIH/3T3 cells. *Nature* 349:426–428.

What is claimed is:

1. A method of identifying a tumor suppressor gene of a cell(s) which comprises:
   a) obtaining cDNA or mRNA from a normal cell(s);
   b) preparing cDNA from the cell(s) if mRNA is obtained in step (a);
   c) preparing a library from the said cDNA, wherein the cDNA is under the control of an inducible expression control system which also carries a selectable gene;
   d) introducing the library into a population of cell(s) expressing a transformed phenotype;
   e) placing the introduced transformed cell(s) from step (d) in conditions permitting expression of the cDNA and an effective concentration of an appropriate selection agent to select the cell(s) expressing the selectable gene;
   f) identifying the cell(s) which express the normal phenotype; and
   g) analyzing the cell(s) so identified so as to characterize the DNA and thus identify the tumor suppressor gene.

2. The method of claim 1, wherein the inducible expression control system comprises an inducible promoter.

3. The method of claim 1, wherein the inducible expression control system comprises a repressible promoter.

4. The method of c claim 1, wherein the cell(s) identified in step (f) are isolated and cultured under conditions so as to isolate and characterize the DNA and thus identify the tumor suppressor gene.

5. The method of claim 1, wherein the cells expressing an transformed phenotype are CREF or CREF Trans 6.

6. The method of claim 5, wherein the CREF cells or CREF Trans 6 cells are transformed by either an adenovirus type 5 or the E1A region of the adenovirus type 5.

7. The method of claim 1, wherein the cells expressing a transformed phenotype are transformed by an adenovirus or a retrovirus.

8. The method of claim 4, wherein the inducer is removed from the cell(s) identified and isolated in step (f) prior to culturing the cell(s).

9. The method of claim 2, wherein the inducible promoter is $Zn^{2+}$ metallothionein promoter, metallothionein-1 promoter, human metallothionein IIA promoter, lac promoter, lacO promoter, mouse mammary tumor virus early promoter, mouse mammary tumor virus LTR promoter, triose dehydrogenase promoter, herpes simplex virus thymidine kinase promoter, simian virus 40 early promoter or retroviral myeloproliferative sarcoma virus promoter.

10. The method of claim 9, wherein the inducible promoter is a mouse mammary tumor virus early promoter.

11. The method of claim 1, wherein the selectable gene is neomycin phosphotransferase, hygromycin, puromycin, G418 resistance, histidinol dehydrogenase or dihydrofolate reductase gene.

12. The method of claim 11, wherein the selectable gene is a neomycin phosphtransferase gene.

13. The method of claim 1, wherein the transformed cells in step (d) are transformed by at least one oncogene.

14. The method of claim 13, wherein the oncogene is H-ras, K-ras, N-ras, v-src, v-raf, HPV-18 or HPV-51.

15. The method of claim 1, wherein the transformed cells in step (d) are transformed by multiple oncogenes.

16. A method of identifying a tumor suppressor gene of a cell(s) which comprises:
   a) obtaining cDNA or mRNA from a normal cell(s);
   b) preparing cDNA from the cell(s) if mRNA is obtained in step (a)
   c) preparing an antisense library from the said cDNA, wherein the cDNA is under the control of an inducible expression control system which also carries a selectable gene;
   d) introducing the antisense library into a population of normal cell(s);
   e) placing the transfected normal cell(s) from step (d) in condition permitting expression of the antisense cDNA and an effective concentration of an appropriate selection agent to select the cell(s) expressing the selectable gene;
   f) identifying the cell(s) which express the transformed phenotype; and
   g) analyzing the transformed cell(s) so identified so as to characterize the antisense cDNA and thus identify the corresponding tumor suppressor gene.

17. The method of claim 16, wherein the cell(s) identified in step (f) are cultured under conditions so as to isolate and characterize the DNA and thus identify the tumor suppressor gene.

18. A method of identifying a gene in a cell(s) associated with an unknown genetic defect having a characteristic phenotype, which comprises:
   a) obtaining cDNA or mRNA from a normal cell(s);
   b) preparing cDNA from cell(s) if mRNA is obtained in step (a);
   c) preparing a library from the said cDNA, wherein the cDNA is under the control of an inducible expression control system which also carries a selectable gene;

d) introducing the library into a population of cell(s) containing the unknown genetic defect having a characteristic phenotype;

e) placing the cell(s) from step (d) in conditions permitting expression of the cDNA and an effective concentration of an appropriate selection agent to select the cell(s) expressing the selectable gene;

f) identifying the cell(s) which express a normal phenotype; and g) analyzing the cell(s) so identified so as to characterize the DNA and thus identify the gene associated with the unknown genetic defect.

19. The method of claim 18, wherein the cell(s) identified in step (f) are isolated and cultured under conditions so as to isolate and characterize the DNA and thus identify the gene associated with the unknown genetic defect.

20. The method of claim 18, wherein the cell(s) having an unknown genetic defect is a cell(s) from a human tumor cell line.

21. The method of claim 18, wherein the cell(s) having an unknown genetic defect is a cell(s) from primary human tumor isolates.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

TATTCTATTA CAGCTCAGTC CACG                                        24

(2) INFORMATION FOR SEQ ID NO:2:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:2:

AGGCTTCTTC TTTTCCACTG GTGT                                        24

(2) INFORMATION FOR SEQ ID NO:3:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:3:

CTGCGTCGTT GGAGTCTTTC C                                            21

(2) INFORMATION FOR SEQ ID NO:4:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:4:

TTGAGGATCC AACACGGCGA                                              20

(2) INFORMATION FOR SEQ ID NO:5:

(i) SEQUENCE CHARACTERISTICS:
      (A) LENGTH: 29 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:5:

-continued

```
GGGAATTCCT TCACAGTCCA TCGCCGTTG                                            29

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GGGGGATCCA ACACCATGTT CGAAGACAAG                                           30
```